United States Patent
Pai et al.

(10) Patent No.: US 11,731,936 B2
(45) Date of Patent: Aug. 22, 2023

(54) DIISOCYANATE COMPOSITION, PREPARATION METHOD THEREOF AND OPTICAL MATERIAL USING SAME

(71) Applicants: SKC CO., LTD., Gyeonggi-do (KR); WOORI FINE CHEM CO., LTD., Gyeonggi-do (KR)

(72) Inventors: Jaeyoung Pai, Gyeonggi-do (KR); Jeongmoo Kim, Gyeonggi-do (KR); Jung Hwan Myung, Gyeonggi-do (KR); Hyuk Hee Han, Gyeonggi-do (KR); Jooyoung Jung, Gyeonggi-do (KR); Myung-Ok Kyun, Gyeonggi-do (KR)

(73) Assignees: SKC CO., LTD., Gyeonggi-do (KR); WOORI FINE CHEM CO., LTD, Gyeonggi-do (KR)

( * ) Notice: Subject to any disclaimer, the term of this patent is extended or adjusted under 35 U.S.C. 154(b) by 215 days.

(21) Appl. No.: 17/111,857

(22) Filed: Dec. 4, 2020

(65) Prior Publication Data

US 2021/0171448 A1 Jun. 10, 2021

(30) Foreign Application Priority Data

| Dec. 6, 2019 | (KR) | 10-2019-0161537 |
| Dec. 6, 2019 | (KR) | 10-2019-0162101 |
| Apr. 14, 2020 | (KR) | 10-2020-0045442 |
| May 7, 2020 | (KR) | 10-2020-0054559 |

(51) Int. Cl.
| *C07C 263/20* | (2006.01) |
| *G02B 1/04* | (2006.01) |
| *C08G 18/38* | (2006.01) |
| *C08G 18/75* | (2006.01) |
| *C07C 265/14* | (2006.01) |

(52) U.S. Cl.
CPC ........ *C07C 263/20* (2013.01); *C08G 18/3868* (2013.01); *C08G 18/757* (2013.01); *G02B 1/041* (2013.01); *C07C 265/14* (2013.01)

(58) Field of Classification Search
CPC ... C07C 263/10; C07C 263/20; C07C 265/14; C07C 209/74; C07C 211/12; C07C 211/18; C07C 211/51; C07C 2601/14; C07C 265/04; C07C 265/08; C08G 18/3868; C08G 18/3876; C08G 18/73; C08G 18/755; C08G 18/757; C08G 18/7642; C08G 18/246; C08G 18/3855; C08G 18/3874; C08G 18/72; C08G 18/753; G02B 1/041; B29D 11/00009; C08L 75/04; C08L 81/00; Y02P 20/582
See application file for complete search history.

(56) References Cited

U.S. PATENT DOCUMENTS

| 3,211,631 | A | * | 10/1965 | Fuchs | C07C 7/06 203/77 |
| 3,492,331 | A | * | 1/1970 | Ulrich | C07C 263/10 548/569 |
| 2012/0101299 | A1 | * | 4/2012 | Schelling | C07C 263/10 560/347 |
| 2019/0106529 | A1 | * | 4/2019 | Kuma | C08G 18/773 |
| 2021/0230352 | A1 | * | 7/2021 | Kim | C07C 209/90 |

FOREIGN PATENT DOCUMENTS

| CN | 1931834 A | | 3/2007 |
| CN | 106674056 A | | 5/2017 |
| CN | 106748887 | * | 5/2017 |
| CN | 112292413 A | | 1/2021 |
| KR | 1994-0001948 B1 | | 3/1994 |
| KR | 101954346 B1 | | 3/2019 |
| WO | WO2017179575 | * | 10/2017 |

OTHER PUBLICATIONS

CN106748887 translation 5 pages (Year: 2017).*
Office Action for application 202011430121.1 issued by the Chinese Patent Office dated May 31, 2022.
Office Action issued in corresponding Korean Patent Application No. 10-2020-0045442, dated Jul. 20, 2021, 6 pages, by the Korean Intellectual Property Office.

* cited by examiner

*Primary Examiner* — Yevgeny Valenrod
*Assistant Examiner* — Blaine G Doletski
(74) *Attorney, Agent, or Firm* — IP & T Group LLP

(57) ABSTRACT

In the embodiments, an aqueous hydrochloric acid solution instead of hydrogen chloride gas and solid triphosgene instead of phosgene gas may be used in the process of preparing a diisocyanate from a diamine through a diamine hydrochloride. In addition, the embodiments provide processes for preparing a diisocyanate composition and an optical lens of high quality in which the content of water, the content of cations, or the content of an aromatic compound containing 3 or more of chlorine (Cl) in the organic solvent used in the reaction of a diamine hydrochloride composition and triphosgene is adjusted to a specific range.

11 Claims, 2 Drawing Sheets

[Fig. 1A]
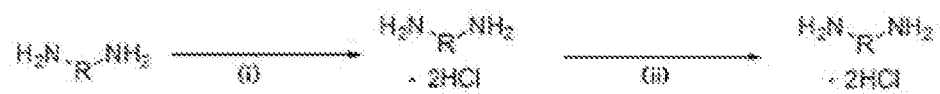
[Fig. 1B]
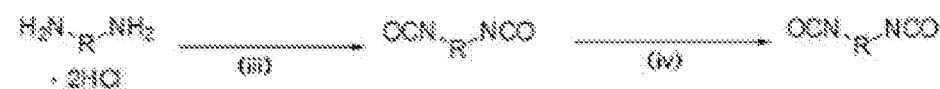
[Fig. 2]
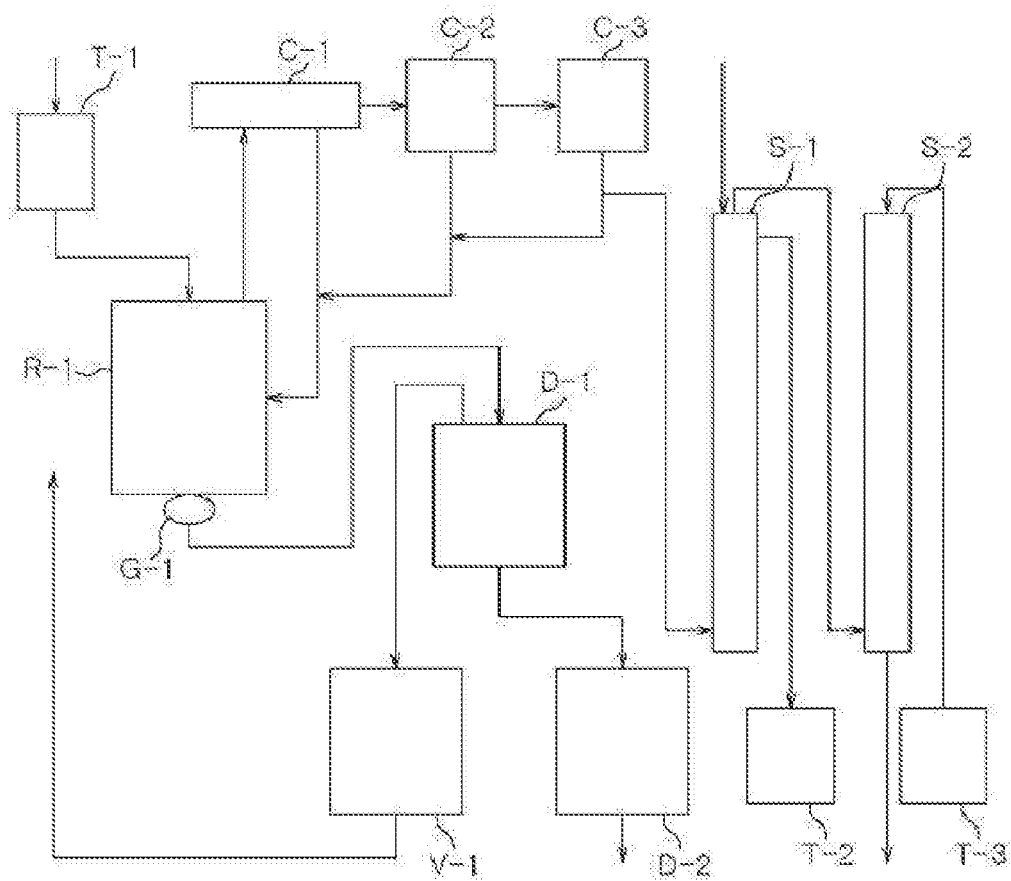

[Fig. 3]
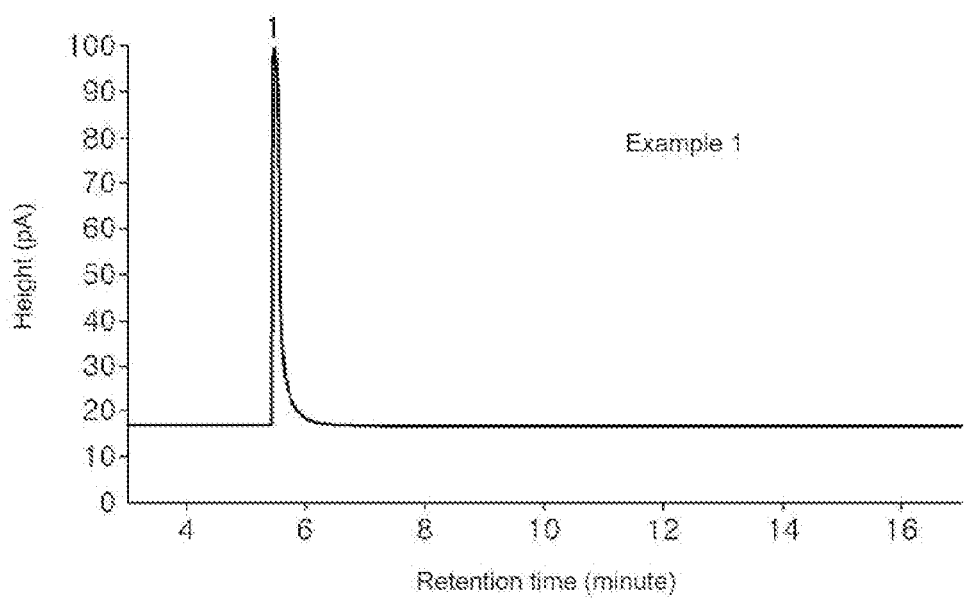
[Fig. 4]
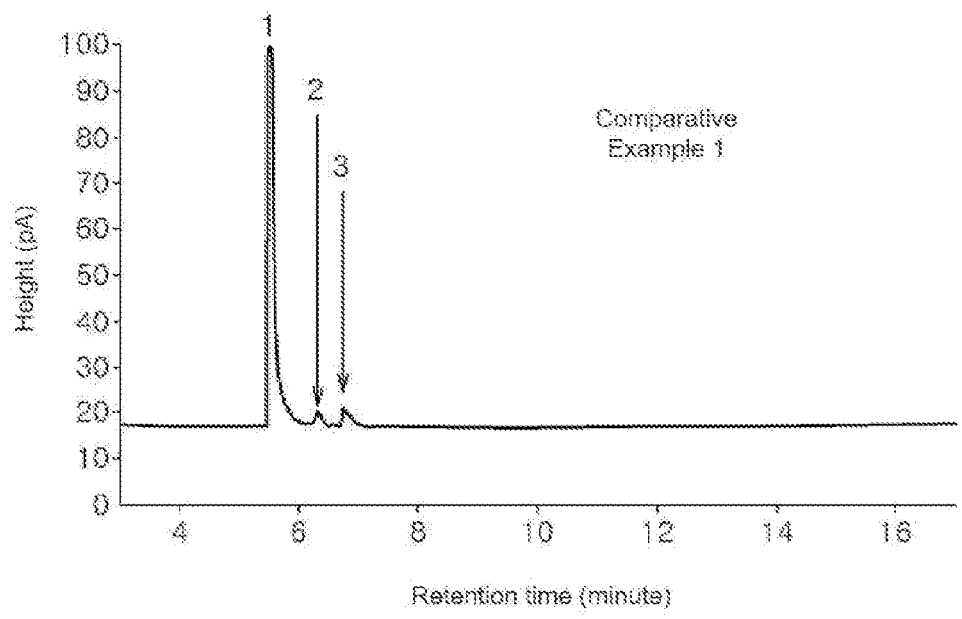

DIISOCYANATE COMPOSITION, PREPARATION METHOD THEREOF AND OPTICAL MATERIAL USING SAME

The present application claims priority of Korean patent application numbers 10-2019-0161537 filed on Dec. 6, 2019, 10-2019-0162101 filed on Dec. 6, 2019, 10-2020-0045442 filed on Apr. 14, 2020 and 10-2020-0054559 filed on May 7, 2020. The disclosure of each of the foregoing applications is incorporated herein by reference in its entirety.

TECHNICAL FIELD

Embodiments relate to a diisocyanate composition, a process for preparing the same, an optical material using the same. More specifically, the embodiments relate to a process for preparing a diisocyanate composition using a diamine hydrochloride composition, a diisocyanate composition prepared thereby, and an optical lens using the same.

BACKGROUND ART

Since plastics optical materials are lightweight, hardly breakable, and excellent in dyeability as compared with optical materials made of inorganic materials such as glass, plastic materials of various resins are widely used as optical materials for eyeglass lenses, camera lenses, and the like. In recent years, there has been an increased demand for higher performance of optical materials, particularly in terms of high transparency, high refractive index, low specific gravity, high thermal resistance, high impact resistance, and the like.

Isocyanates used as a raw material for plastic optical lenses are prepared by a phosgene method, a non-phosgene method, a pyrolysis method, or the like.

In the phosgene method, an amine as a raw material is reacted with phosgene ($COCl_2$) gas to synthesize an isocyanate. In addition, in the non-phosgene method, xylylene chloride is reacted with sodium cyanate in the presence of a catalyst to synthesize an isocyanate. In the pyrolysis method, an amine is reacted with an alkyl chloroformate to prepare a carbamate, which is pyrolyzed in the presence of a catalyst at a high temperature to synthesize an isocyanate.

The phosgene method among the above methods for preparing isocyanates is the most widely used. In particular, a direct method in which an amine is directly reacted with phosgene gas has been commonly used. But it has a problem that a plurality of apparatuses for the direct reaction of phosgene gas are required. Meanwhile, in order to supplement the direct method, a hydrochloride method has been developed in which an amine is reacted with hydrogen chloride gas to obtain an amine hydrochloride as an intermediate, which is reacted with phosgene, as disclosed in Korean Patent Publication No. 1994-0001948.

In the method of obtaining hydrochloride as an intermediate by reacting an amine with hydrogen chloride gas among the conventional phosgene methods for synthesizing isocyanates, a hydrochloride is produced as fine particles at atmospheric pressure, so that the agitation inside the reactor is not smoothly carried out. Thus, an additional process of raising the temperature to increase the pressure inside the reactor is required, and there is a problem that the yield of the final product is low as well.

In addition, phosgene gas used in the conventional phosgene method is highly toxic and is a substance subject to environmental regulations. There is a difficulty in storage and management since a separate cooling apparatus is required to store it.

In addition, polythiourethanes are widely used as an optical material by virtue of their excellent optical characteristics and excellent mechanical properties. A polythiourethane may be prepared by reacting a thiol and an isocyanate. Lenses made from a polythiourethane are widely used by virtue of their high refractive index, lightweight, and relatively high impact resistance.

Isocyanates used as a raw material of a polythiourethane are capable of producing polythiourethanes having different structures depending on the number and position of the functional groups in the isocyanates. Thus, the isocyanates have a significant impact on the physical properties of a product produced from the polythiourethane. Accordingly, a certain kind of isocyanate that can impart the desired properties to a final product is used.

In particular, since xylylene diisocyanate (XDI) has both characteristics of alicyclic isocyanates (e.g., resistance to yellowing, readily controllable reactivity, and the like) and those of aliphatic isocyanates (e.g., excellent mechanical properties, high refractive indices, and the like), it is advantageously used as an optical material.

Xylylene diisocyanate is classified into orthoxylylene diisocyanate (o-XDI), metaxylylene diisocyanate (m-XDI), and paraxylylene diisocyanate (p-XDIA) depending on the relative position of the diisocyanate groups. m-XDI among these is the most widely used as a raw material for an optical lens since it is suitable for the physical properties of an optical lens and available in the market.

However, even when m-XDI is used for an optical material, there is a limit in achieving satisfactory optical characteristics due to the occurrence of striae, cloudiness, or yellowing in the optical material. Even if the optical characteristics in terms of striae, cloudiness, or yellow index are satisfied, the impact resistance may be deteriorated. There may arise a problem that the purity and yield of the diisocyanate composition or the final product may be reduced.

Accordingly, in order to achieve an optical material of high quality by solving the above problems, there is an urgent demand for developing a diisocyanate composition or a process for preparing the same.

DETAILED DESCRIPTION OF THE INVENTION

Technical Problem

Accordingly, the present inventors have been able to solve the conventional environmental, yield, and quality problems in the process of preparing a diisocyanate, which is mainly used as a raw material for plastic optical lenses, from a diamine through a hydrochloride thereof by way of using an aqueous hydrochloric acid solution instead of hydrogen chloride gas and solid triphosgene instead of phosgene gas while adjusting the reaction conditions.

In addition, the present inventors have focused that the organic solvent used in the reaction of a diamine hydrochloride composition and triphosgene may contain water during the reaction, transport, and storage. Such water reacts with triphosgene to reduce the number of equivalents for the reaction, and it also reacts with a diisocyanate to form urea, which significantly reduces the yield and purity of the final product.

Accordingly, an object of the embodiments is to provide processes for preparing a diisocyanate composition and an optical lens of high quality in which the content of water in the organic solvent used in the reaction of a diamine hydrochloride composition and triphosgene is adjusted to a specific range.

In addition, the present invention is designed to solve the problems of the prior art. It has been discovered that the yield and purity of a diisocyanate composition as well as the physical properties of an optical material prepared using the same can be effectively satisfied when the total content of cations or the content of an aromatic compound containing 3 or more of chlorine (Cl) in an organic solvent is adjusted to a specific level or less in the preparation of a diisocyanate composition.

Accordingly, an object of the embodiments is to provide a diisocyanate composition of high quality in which the total content of cations or the content of an aromatic compound containing 3 or more of chlorine (Cl) in an organic solvent is adjusted in the preparation of a diisocyanate composition, thereby preventing the occurrence of striae and cloudiness in an optical material, lowering the yellow index, and enhancing the transmittance, and a process for preparing the same.

Another object of the embodiments is to provide an optical material of high quality prepared from the diisocyanate composition and a process for preparing the same.

Solution to the Problem

According to an embodiment, there is provided a process for preparing a diisocyanate composition, which comprises (1) reacting a diamine with an aqueous hydrochloric acid solution to obtain a diamine hydrochloride composition; and (2) reacting the diamine hydrochloride composition with triphosgene in an organic solvent to obtain a diisocyanate composition, wherein the content of water, the content of cations, or the content of an aromatic compound containing 3 or more of chlorine (Cl) in the organic solvent is adjusted.

According to another embodiment, there is provided an optical material, which comprises a polythiourethane polymerized from a diisocyanate composition and a thiol or an episulfide, wherein the diisocyanate composition is obtained by reacting a diamine hydrochloride composition and triphosgene in an organic solvent, and the organic solvent comprises an aromatic compound containing 3 or more of chlorine (Cl) in an amount of 5,000 ppm or less.

According to still another embodiment, there is provided a diisocyanate composition, which comprises a diisocyanate, wherein the total content of cations in the composition is 100 ppm or less, the composition is obtained by reacting a diamine hydrochloride composition and triphosgene in an organic solvent, and the total content of cations in the organic solvent is adjusted to 1 ppm to 5 ppm.

Advantageous Effects of the Invention

In the process for preparing a diisocyanate according to the above embodiment, phosgene gas, which is highly toxic and has difficulties in storage and management, is not used. Instead, triphosgene, which is less toxic and does not require a separate cooling storage apparatus since it is solid at room temperature, is used; thus, it is excellent in the handling convenience and processability. In addition, in the process for preparing a diisocyanate according to the above embodiment, an aqueous hydrochloric acid solution, without the use of hydrogen chloride gas, is used to prepare a diamine hydrochloride as an intermediate. Since the reaction can be carried out even at atmospheric pressure, an additional apparatus for high-temperature heating and cooling is not required, and the yield can be enhanced.

In addition, in the process for preparing a diisocyanate composition according to the above embodiment, an aqueous hydrochloric acid solution is used to prepare a diamine hydrochloride composition, so that the final yield can be further enhanced. The selection of raw materials can be broadened since the content of water and impurities in the diamine as a raw material has little impact.

In particular, according to the embodiment, the content of water, the content of cations, or the content of an aromatic compound containing 3 or more of chlorine (Cl) in the organic solvent used in the reaction of a diamine hydrochloride composition and triphosgene is adjusted within a specific range, so that the formation of urea during the phosgenation reaction can be suppressed, thereby preventing a deterioration in the physical properties of the final optical lens in terms of stria, cloudiness, and yellow index.

In addition, the content of water contained in the organic solvent during the reaction, transport, and storage is reduced. Even if the organic solvent is recovered after the reaction and then recycled for the next reaction, the quality of the product may not be deteriorated. In addition, even if a recycled organic solvent is used, an optical material of high quality can be obtained when purification is performed under a specific condition, whereby the content of cations or an aromatic compound containing 3 or more of chlorine (Cl) in the organic solvent is adjusted to the specific level.

Accordingly, the process for preparing a diisocyanate composition according to the embodiment can be applied to the preparation of a plastic optical lens of high quality.

BRIEF DESCRIPTION OF THE DRAWINGS

FIG. 1A and FIG. 1B schematically show the process for preparing a diisocyanate composition according to an embodiment.

FIG. 2 shows an example of the process equipment for the reaction of a diamine hydrochloride and triphosgene.

FIG. 3 is a graph showing the result of measuring 1,2-dichlorobenzene (ODCB) used in Example 1 by gas chromatography (GC).

FIG. 4 is a graph showing the result of measuring 1,2-dichlorobenzene (ODCB) used in Comparative Example 1 by gas chromatography (GC).

REFERENCE NUMERALS OF THE DRAWINGS

T-1: first tank, T-2: second tank, T-3: third tank
R-1: reactor, D-1: first distiller, D-2: second distiller
C-1: first condenser, C-2: second condenser, C-3: third condenser
S-1: first scrubber, S-2: second scrubber
G-1: viewing window, V-1: solvent recovery apparatus.

BEST MODE FOR CARRYING OUT THE INVENTION

Throughout the present specification, when a part is referred to as "comprising" an element, it is understood that other elements may be comprised, rather than other elements are excluded, unless specifically stated otherwise.

In addition, all numbers and expression related to the physical properties, contents, dimensions, and the like used herein are to be understood as being modified by the term "about," unless otherwise indicated.

In the present specification, an "amine" refers to a compound having one or more amine groups at the terminal, and a "diamine" refers to a compound having two amine groups at the terminal. They may have a wide variety of structures depending on the skeleton of an aliphatic chain, an aliphatic ring, and an aromatic ring. Specific examples of the diamine include xylylenediamine (XDA), hexamethylenediamine (HDA), 2,2-dimethylpentanediamine, 2,2,4-trimethylhexanediamine, butenediamine, 1,3-butadiene-1,4-diamine, 2,4,4-trimethylhexamethylenediamine, bis(aminoethyl)carbonate, 4,4'-methylenediamine (MDA), bis(aminoethyl) ether, bis(aminoethyl)benzene, bis(aminopropyl)benzene, α,α,α',α'-tetramethylxylylenediamine, bis(aminobutyl)benzene, bis(aminomethyl)naphthalene, bis(aminomethyl)diphenyl ether, bis(aminoethyl)phthalate, 2,6-di(aminomethyl)furan, hydrogenated xylylenediamine (H6XDA), dicyclohexylmethanediamine, cyclohexanediamine, methylcyclohexanediamine, isophoronediamine (IPDA), dicyclohexyldimethylmethanediamine, 2,2-dimethyldicyclohexylmethanediamine, 2,5-bis(aminomethyl)bicyclo-[2,2,1]-heptane,2,6-bis(aminomethyl)bicyclo-[2,2,1]-heptane, 3,8-bis(aminomethyl)tricyclodecane, 3,9-bis(aminomethyl)tricyclodecane, 4,8-bis(aminomethyl)tricyclodecane, 4,9-bis(aminomethyl)tricyclodecane, norbornenediamine (NBDA), bis(aminomethyl) sulfide, bis(aminoethyl) sulfide, bis(aminopropyl) sulfide, bis(aminohexyl) sulfide, bis(aminomethyl) sulfone, bis(aminomethyl) disulfide, bis(aminoethyl) disulfide, bis(aminopropyl) disulfide, bis(aminomethylthio) methane, bis(aminoethylthio)methane, bis(aminomethylthio) ethane, and bis(aminomethylthio)ethane. More specifically, the diamine may be at least one selected from the group consisting of xylylenediamine (XDA), norbornenediamine (NBDA), hydrogenated xylylenediamine (H6XDA), isophoronediamine (IPDA), and hexamethylenediamine (HDA). The xylylenediamine (XDA) includes orthoxylylenediamine (o-XDA), metaxylylenediamine (m-XDA), and paraxylylenediamine (p-XDA).

In the present specification, an "isocyanate" refers to a compound having an NCO group, a "diisocyanate" refers to a compound having two NCO groups at the terminal. They may have a wide variety of structures depending on the skeleton of an aliphatic chain, an aliphatic ring, and an aromatic ring. Specific examples of the diamine include xylylene diisocyanate (XDI), hexamethylene diisocyanate (HDI), 2,5-bis(isocyanatomethyl)-bicyclo[2.2.1]heptane, 2,6-bis(isocyanatomethyl)-bicyclo[2.2.1]heptane, hydrogenated xylylene diisocyanate (H6XDI), dicyclohexylmethane diisocyanate, isophorone diisocyanate (IPDI), 1,2-diisocyanatobenzene, 1,3-diisocyanatobenzene, 1,4-diisocyanatobenzene, 2,4-diisocyanatotoluene, ethylphenylene diisocyanate, dimethylphenylene diisocyanate, biphenyl diisocyanate, toluidine diisocyanate, 4,4'-methylenebis(phenylisocyanate) (MDI), 1,2-bis(isocyanatomethyl)benzene, 1,3-bis(isocyanatomethyl)benzene, 1,4-bis(isocyanatomethyl)benzene, 1,2-bis(isocyanatoethyl)benzene, 1,3-bis(isocyanatoethyl)benzene, 1,4-bis(isocyanatoethyl)benzene, α,α,α',α'-tetramethylxylylene diisocyanate, bis(isocyanatomethyl)naphthalene, bis(isocyanatomethylphenyl) ether, norbornene diisocyanate (NBDI), bis(isocyanatomethyl) sulfide, bis(isocyanatoethyl) sulfide, bis(isocyanatopropyl) sulfide, 2,5-diisocyanatotetrahydrothiophene, 2,5-diisocyanatomethyltetrahydrothiophene, 3,4-diisocyanatomethyltetrahydrothiophene, 2,5-diisocyanato-1,4-dithiane, and 2,5-diisocyanatomethyl-1,4-dithiane. More specifically, the diisocyanate may be at least one selected from the group consisting of xylylene diisocyanate (XDI), norbornene diisocyanate (NBDI), hydrogenated xylylene diisocyanate (H6XDI), isophorone diisocyanate (IPDI), and hexamethylene diisocyanate (HDI). The xylylene diisocyanate (XDI) includes orthoxylylene diisocyanate (o-XDI), metaxylylene diisocyanate (m-XDI), and paraxylylene diisocyanate (p-XDIA).

In the present specification, as is well known, a "composition" may refer to a form in which two or more chemical components are mixed or combined in a solid, liquid, and/or gas phase while generally maintaining their respective unique properties.

The compounds used in each reaction step according to the above embodiment (e.g., triphosgene) or the compounds obtained as a result of the reaction (e.g., diamine hydrochloride, diisocyanate) are generally present in a mixed or combined state with heterogeneous components generated as unreacted raw materials in each reaction step, as side reactions or reaction with water, or as natural decomposition of the compounds. A trace amount of these components may remain to exist with the main components.

According to the embodiment, since attention is paid to these heterogeneous components mixed or combined with the main compounds, even a trace amount of the heterogeneous components is treated as a composition mixed or combined with the main compounds to specifically illustrate the components and contents thereof.

In addition, in the present specification, for clear and easy distinction between various compositions, terms are also described in combination with the names of the main components in the composition. For example, a "diamine hydrochloride composition" refers to a composition comprising a diamine hydrochloride as a main component, and a "diisocyanate composition" refers to a composition comprising a diisocyanate as a main component. In such event, the content of the main component in the composition may be 50% by weight or more, 80% by weight or more, or 90% by weight or more, for example, 90% by weight to 99.9% by weight.

In this specification, the unit of ppm refers to ppm by weight.

[Process for Preparing a Diisocyanate Composition]

The process for preparing a diisocyanate composition according to an embodiment comprises (1) reacting a diamine with an aqueous hydrochloric acid solution to obtain a diamine hydrochloride composition; and (2) reacting the diamine hydrochloride composition with triphosgene in an organic solvent to obtain a diisocyanate composition, wherein the content of water, the content of cations, or the content of an aromatic compound containing 3 or more of chlorine (Cl) in the organic solvent is adjusted.

Specifically, the content of water in the organic solvent may be 200 ppm or less, the organic solvent may comprise an aromatic compound containing 3 or more of chlorine (Cl) in an amount of 5,000 ppm or less, and the total content of cations in the organic solvent may be adjusted to 1 ppm to 5 ppm.

FIG. 1A and FIG. 1B schematically show the process for preparing a diisocyanate composition according to an embodiment. In FIG. 1A and FIG. 1B, R comprises an aromatic ring, an aliphatic ring, an aliphatic chain, and the like. As a specific example, R may be xylylene, norbornene, hydrogenated xylylene, isophorone, or hexamethylene, but it is not limited thereto.

In FIG. 1A, (i) may comprise a step of adding an aqueous hydrochloric acid solution to react a diamine with the aqueous hydrochloric acid solution. In FIG. 1A, (ii) may comprise at least one step selected from a precipitation step, a filtration step, a drying step, and a washing step. In FIG.

1B, (iii) may comprise a step of adding triphosgene to react a diamine hydrochloride composition with triphosgene. In FIG. 1B, (iv) may comprise at least one step selected from a degassing step, a filtration step, and a distillation step.

Hereinafter, each step will be described in detail.

Preparation of a Diamine Hydrochloride Composition

First, a diamine is reacted with an aqueous hydrochloric acid solution to obtain a diamine hydrochloride composition. In addition, after the reaction of a diamine and an aqueous hydrochloric acid solution, a first organic solvent may be further added to obtain the diamine hydrochloride composition in a solid phase.

The following Reaction Scheme 1 shows an example of the reaction in this step.

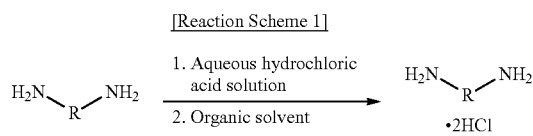

[Reaction Scheme 1]

In the above scheme, R comprises an aromatic ring, an aliphatic ring, an aliphatic chain, and the like. As a specific example, R may be xylylene, norbornene, hydrogenated xylylene, isophorone, or hexamethylene, but it is not limited thereto.

In the conventional method in which hydrogen chloride gas is used, a hydrochloride is produced as fine particles upon the reaction at atmospheric pressure, so that the agitation inside the reactor is not smoothly carried out. Thus, an additional process of raising the pressure to increase the internal temperature of the reactor is required, and there is a problem that the yield of the final product is low as well.

According to the above embodiment, however, since an aqueous hydrochloric acid solution is used, it is possible to solve the problem involved in the prior art in which hydrogen chloride gas is used. Specifically, when an aqueous hydrochloric acid solution is used, the product obtained through the reaction is in a solid form rather than a slurry form, so that the yield is high. The reaction can be carried out even at atmospheric pressure, so that a separate apparatus or process for rapid cooling is not required.

The concentration of the aqueous hydrochloric acid solution may be 5% by weight to 50% by weight. Within the above concentration range, it is possible to minimize the dissolution of the hydrochloride in the aqueous hydrochloric acid solution, thereby enhancing the final yield, and to improve the handling convenience.

Specifically, the concentration of the aqueous hydrochloric acid solution may be 10% by weight to 45% by weight, 20% by weight to 45% by weight, or 30% by weight to 40% by weight. More specifically, the aqueous hydrochloric acid solution may have a concentration of 20% by weight to 45% by weight.

The diamine and the aqueous hydrochloric acid solution may be introduced to the reaction at an equivalent ratio of 1:2 to 5. If the equivalent ratio is within the above range, it is possible to reduce the unreacted materials and to prevent a decrease in the yield caused by dissolution as water is generated. Specifically, the diamine and the aqueous hydrochloric acid solution may be introduced to the reaction at an equivalent ratio of 1:2 to 2.5.

The introduction of the diamine and the aqueous hydrochloric acid solution may be carried out while the internal temperature of the reactor is maintained to be constant. When the diamine and the hydrochloric acid aqueous solution are introduced, the internal temperature of the reactor may be in the range of 20° C. to 100° C. Within the above temperature range, it is possible to prevent the temperature from being raised above the boiling point, which is not suitable for the reaction, or the temperature from being lowered too much, whereby the reaction efficiency is reduced. Specifically, when the diamine and the hydrochloric acid aqueous solution are introduced, the internal temperature of the reactor may be 20° C. to 60° C., 20° C. to 40° C., or 40° C. to 60° C. More specifically, the diamine and the aqueous hydrochloric acid solution may be introduced to the reaction at an equivalent ratio of 1:2 to 5 at a temperature of 20° C. to 40° C.

In the conventional hydrochloride method, a large amount of heat is generated in the reaction, which requires rapid cooling through a separate cooler, whereas the reaction materials are introduced while a low temperature is maintained according to the above embodiment, which does not require a separate cooler.

The introduction of the diamine and the aqueous hydrochloric acid solution may be carried out, for example, in a sequence in which the hydrochloric acid aqueous solution may be first introduced to the reactor and the diamine may then be slowly introduced to the reactor. The introduction of the diamine and/or the aqueous hydrochloric acid solution may be carried out for 30 minutes to 3 hours.

When the introduction of the diamine and the hydrochloric acid aqueous solution is completed, the internal temperature of the reactor may be lowered to 0° C. to 20° C., 0° C. to 10° C., or 10° C. to 20° C.

The reaction between the diamine and the aqueous hydrochloric acid solution may be carried out at atmospheric pressure for, for example, 30 minutes to 2 hours with stirring.

As a result of the reaction between the diamine and the aqueous hydrochloric acid solution, a diamine hydrochloride composition in an aqueous solution form may be obtained as the reaction resultant.

Thereafter, a step of treating the diamine hydrochloride composition may be further carried out. Specifically, the process may further comprise treating the diamine hydrochloride composition after the diamine hydrochloride composition is obtained and before the diamine hydrochloride composition is reacted with triphosgene.

For example, the step of treating the diamine hydrochloride composition may comprise at least one of precipitating the diamine hydrochloride composition, filtering the diamine hydrochloride composition, drying the diamine hydrochloride composition, and washing the diamine hydrochloride composition.

Specifically, a first organic solvent may be introduced to the reaction resultant to precipitate a solid diamine hydrochloride composition. That is, the first organic solvent may induce the precipitation of a solid diamine hydrochloride composition through crystallization. More specifically, the first organic solvent may be introduced to the reaction resultant, which is cooled and further stirred to carry out the reaction.

Specifically, the first organic solvent may be at least one selected from the group consisting of diethyl ether, diisopropyl ether, dioxane, tetrahydrofuran, methanol, ethanol, dimethyl sulfoxide, dimethylformamide, acetonitrile, acetone, trichloroethylene, tetrachloroethane, trichloroethanol, n-butanol, isobutanol, methyl ethyl ketone, methyl butyl ketone, isopropanol, hexane, chloroform, and methyl acetate.

The amount (weight) of the first organic solvent introduced may be 1 to 5 times the weight of the diamine. If the introduced amount is within the above range, it is possible to prevent the use of excessive organic solvents while the yield of the final hydrochloride is high. Specifically, the first organic solvent may be introduced to the reaction in an amount of 1 to 2 times, 1 to 1.5 times, or 1.3 to 1.5 times, the weight of the diamine.

After the first organic solvent is introduced, the cooling temperature may be −10° C. to 10° C. or −5° C. to 5° C. In addition, the additional reaction time after cooling may be 30 minutes to 2 hours or 30 minutes to 1 hour.

According to a specific example, the steps of (1a) introducing the aqueous hydrochloric acid solution to a first reactor; (1b) introducing the diamine to the first reactor and stirring them; and (1c) introducing the first organic solvent to the first reactor and stirring them may be sequentially carried out.

More specifically, the process may further comprise cooling the inside of the reactor to a temperature of 0° C. to 10° C. after the introduction of the diamine and before stirring in step (1 b); and cooling the inside of the reactor to a temperature of −5° C. to 5° C. after the introduction of the first organic solvent and before stirring in step (1c).

After the first organic solvent is introduced, separation, filtration, washing, and drying may be further carried out. For example, after the first organic solvent is introduced, the aqueous layer may be separated, filtered, washed, and dried to obtain a solid diamine hydrochloride composition. The washing may be carried out one or more times using, for example, a solvent having a polarity index of 5.7 or less. In addition, the drying may be carried out using vacuum drying. For example, it may be carried out at a temperature of 40° C. to 90° C. and a pressure of 2.0 torr or less.

As a result, the impurities generated in the step of obtaining the diamine hydrochloride composition may be removed together with the first organic solvent. Thus, the process may further comprise removing the impurities generated in the step of obtaining the diamine hydrochloride composition together with the first organic solvent. Impurities are generated in the reaction for preparing the diamine hydrochloride composition and are contained in the first organic solvent. Such impurities may be removed by the step of removing the first organic solvent, whereby the purity of the product may be increased.

According to the above process, a diamine is reacted with an aqueous hydrochloric acid solution, which is then subjected to additional treatment such as precipitation, filtration, drying, and washing, whereby a solid diamine hydrochloride composition can be obtained with high purity. In contrast, in the conventional process in which a diamine is reacted with hydrogen chloride gas in an organic solvent, a slurry of a diamine hydrochloride is obtained, which is not readily purified.

The yield of the diamine hydrochloride composition thus obtained may be 50% or more, 65% or more, 80% or more, 85% or more, or 90% or more, specifically 85% to 95% or 88% to 92%.

Meanwhile, the organic layer can be separated from the reactant and recycled as an organic solvent. Thus, the recovery rate of the first organic solvent may be 80% or more, 85% or more, or 90% or more, specifically 80% to 95% or 80% to 82%.

Adjustment of the Content of Water in a Diamine Hydrochloride Composition

The content of water in the diamine hydrochloride composition obtained in the previous step may be adjusted, and it is then introduced to the subsequent reaction. For example, the process may further comprise adjusting the content of water in the diamine hydrochloride composition obtained in the previous step to 700 ppm or less.

The content of water in the diamine hydrochloride composition may be adjusted to, for example, 500 ppm or less, 300 ppm or less, 200 ppm or less, 100 ppm or less, or 50 ppm or less. Specifically, the diamine hydrochloride composition in which the content of water has been adjusted may have a content of water of 100 ppm or less or 50 ppm or less.

The content of water in the diamine hydrochloride composition may be adjusted in advance before it is introduced to the subsequent reaction. That is, the process may further comprise measuring the content of water in the diamine hydrochloride composition before it is introduced to the subsequent reaction.

The content of water in the diamine hydrochloride composition may be adjusted through at least one of washing and drying.

As an example, the content of water in the diamine hydrochloride composition may be adjusted by washing it with a solvent having a polarity index of 3.9 to 5.7. If the solvent used for washing as described above has a polarity index of 3.9 or more, it is miscible with water and effective in removing water. In addition, if it has a polarity index of 5.7 or less, it does not dissolve triphosgene, thereby increasing the yield.

In addition, if the solvent used for washing has a boiling point of 85° C. or lower, it reduces the residual solvents after drying, thereby enhancing the purity and yield of the product. For example, the boiling point of the solvent used for washing may be 30° C. to 85° C.

Specifically, the solvent used for washing may include at least one selected from the group consisting of tetrahydrofuran (THF), ethyl acetate, methyl acetate, methyl ethyl ketone, and acetone. More specifically, the solvent used for washing may include at least one selected from tetrahydrofuran and acetone.

The content of water in the diamine hydrochloride composition may be adjusted by drying it under a reduced pressure. For example, the content of water in the diamine hydrochloride composition may be adjusted by drying under the conditions of a temperature of 40° C. to 90° C. and a pressure of 0.01 torr to 100 torr.

The drying step may be performed after the above washing is first performed. That is, the content of water in the diamine hydrochloride composition, after the washing, may be further adjusted by drying under the conditions of a temperature of 40° C. to 90° C. and a pressure of 0.01 torr to 100 torr.

In the diamine hydrochloride composition, after the drying, the content of the residual solvents used in the washing may be less than 500 ppm or less than 300 ppm, specifically less than 100 ppm.

Preparation of a Diisocyanate Composition

Next, the diamine hydrochloride composition is reacted with triphosgene to obtain a diisocyanate composition. In such event, the reaction of the diamine hydrochloride composition with triphosgene may be carried out in a second organic solvent.

In addition, according to an embodiment of the present invention, the step of obtaining a diisocyanate composition may comprise reacting the diamine hydrochloride composition, treated by a process comprising at least one of precipitation, filtration, drying, and washing, with triphosgene in a second organic solvent. That is, the process may further comprise treating the diamine hydrochloride composition by at least one of precipitation, filtration, drying, and washing before the diamine hydrochloride composition is reacted with triphosgene.

The second organic solvent comprise an aromatic compound containing 3 or more of chlorine (Cl) in an amount of 5,000 ppm or less. Specifically, the content of the aromatic compound containing 3 or more of chlorine (Cl) contained in the second organic solvent may be 4,900 ppm or less, 4,000 ppm or less, 3,000 ppm or less, 0.5 ppm to 5,000 ppm, 0.5 ppm to 4,900 ppm, 0.5 ppm to 4,000 ppm, 0.5 ppm to 3,000 ppm, 0.5 ppm to 2,600 ppm, 0.5 ppm to 1,000 ppm, 0.5 ppm to 500 ppm, 0.5 ppm to 300 ppm, 0.5 ppm to 100 ppm, 0.5 ppm to 50 ppm, or 0.5 ppm to 10 ppm.

When the diisocyanate composition is prepared, the content of an aromatic compound containing 3 or more of chlorine (Cl) in the second organic solvent is adjusted to the above range, whereby it is possible to enhance the yield and purity of the diisocyanate composition and to enhance the transmittance while preventing the occurrence of yellowing, striae, and cloudiness when applied to an optical material. If the content of an aromatic compound containing 3 or more of chlorine (Cl) contained in the second organic solvent exceeds 5,000 ppm, the yield and purity of the diisocyanate composition may be deteriorated, cloudiness may occur when an optical material is prepared, and the optical characteristics such as transmittance and yellow index may be deteriorated.

The content range of an aromatic compound containing 3 or more of chlorine (Cl) is the content in the second organic solvent used in the preparation of the diisocyanate composition according to the embodiment of the present invention. This content may be adjusted in advance before the second organic solvent is introduced to the reaction.

In order to adjust the content of an aromatic compound containing 3 or more of chlorine (Cl) contained in the second organic solvent to 5,000 ppm or less, the process may further comprise measuring the content of an aromatic compound containing 3 or more of chlorine (Cl) contained in the second organic solvent before the diamine hydrochloride composition is reacted with triphosgene.

The content of an aromatic compound containing 3 or more of chlorine (Cl) contained in the second organic solvent may be measured by, for example, gas chromatography (GC).

As a result of the measurement, if the content of an aromatic compound containing 3 or more of chlorine (Cl) contained in the second organic solvent exceeds 5,000 ppm, the second organic solvent may be purified to adjust the content of the aromatic compound containing 3 or more of chlorine (Cl) to 5,000 ppm or less. The second organic solvent containing an aromatic compound containing 3 or more of chlorine (Cl) whose content has been adjusted as described above may be used in the reaction.

In addition, as a result of the measurement, if the content of an aromatic compound containing 3 or more of chlorine (Cl) contained in the second organic solvent is 5,000 ppm or less, the second organic solvent, as it is, may be introduced into the reaction without purification thereof.

The purification may comprise a purification process by primary distillation under the conditions of a temperature of 45° C. to 75° C. and a pressure of 0.1 torr to 1 torr. Alternatively, the purification may comprise a purification process by primary distillation under the conditions of a temperature of 50° C. to 65° C. and a pressure of 0.1 torr to 1 torr. The purification may be carried out for 2 hours to 15 hours, 5 hours to 10 hours, or 6 hours to 9 hours, under the above conditions.

According to an embodiment of the present invention, the content of an aromatic compound containing 3 or more of chlorine (Cl) in the second organic solvent after the above purification may be adjusted to 100 ppm or less, 50 ppm or less, 30 ppm or less, 20 ppm or less, or 10 ppm or less.

According to an embodiment of the present invention, the second organic solvent may be specifically at least one selected from the group consisting of benzene, toluene, ethylbenzene, chlorobenzene, monochlorobenzene, 1,2-dichlorobenzene, dichloromethane, 1-chloro-n-butane, 1-chloro-n-pentane, 1-chloro-n-hexane, chloroform, carbon tetrachloride, n-pentane, n-hexane, n-heptane, n-octane, cyclohexane, cyclopentane, cyclooctane, and methylcyclohexane. More specifically, the second organic solvent may comprise 1,2-dichlorobenzene (ODCB).

1,2-dichlorobenzene (ODCB), among the second organic solvents, is a solvent widely used in a phosgenation reaction (i.e., reaction of a diamine hydrochloride composition and triphosgene) by virtue of its high boiling point and structure containing chlorine (Cl). However, the control of the purity of the second solvent is very important to increase the purity and yield of the diisocyanate composition.

The second organic solvent, specifically 1,2-dichlorobenzene (ODCB), may be chlorinated by heat, UV, a catalyst, or the like during the reaction as shown in Scheme A below or in an external environment, so that an aromatic compound containing 3 or more of chlorine (Cl), for example, 1,2,3-trichlorobenzene and/or 1,2,4-trichlorobenzene may be produced.

[Reaction Scheme A]

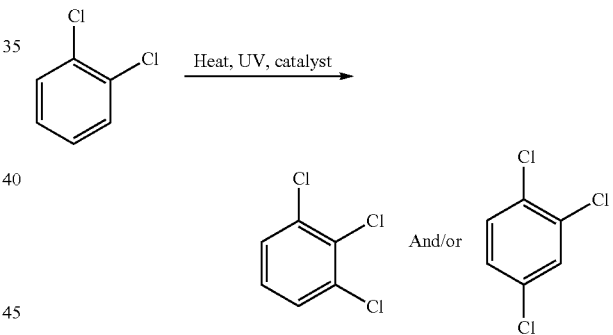

Since the second organic solvent may be recycled to be used after the phosgenation reaction, the control of the aromatic compound containing 3 or more of chlorine (Cl) to a specific content may be a measure for the control of the second organic solvent. It is very important to adopt such a measure for the control in the preparation of a diisocyanate composition for an optical purpose.

In the present invention, it is confirmed that if the content of an aromatic compound containing 3 or more of chlorine (Cl) in the second organic solvent is adjusted to a specific range to control the quality of the second organic solvent, a diisocyanate composition and an optical material of high quality can be produced.

In addition, it is confirmed that, in the present invention, the content of cations contained in the second organic solvent is adjusted to a specific range to control the quality of the second organic solvent, a diisocyanate composition and an optical material of high quality can be produced.

In addition, even if a recycled organic solvent is used, a diisocyanate composition and an optical material of high quality can be obtained when purification is performed under a specific condition, whereby the content of an aromatic compound containing 3 or more of chlorine (Cl) in the second organic solvent can be adjusted.

According to an embodiment of the present invention, the aromatic compound containing 3 or more of chlorine (Cl) may comprise 1,2,3-trichlorobenzene, 1,2,4-trichlorobenzene, or a mixture thereof.

When the aromatic compound containing 3 or more of chlorine (Cl) comprises 1,2,3-trichlorobenzene, 1,2,4-trichlorobenzene, or a mixture thereof, the weight ratio of 1,2,3-trichlorobenzene and 1,2,4-trichlorobenzene may be 1:0.0001 to 0.5, 1:0.0001 to 0.3, 0.0001 to 0.2, or 0.0001 to 0.1.

In addition, according to an embodiment of the present invention, when the second organic solvent is measured by gas chromatography (GC), only the main peak for 1,2-dichlorobenzene (ODCB), which is the second organic solvent, may be present, and an aromatic compound containing 3 or more of chlorine (Cl) may not be contained.

In addition, according to an embodiment of the present invention, when the second organic solvent is measured by gas chromatography (GC), a peak having an area of 0.5(%) or less, 0.3(%) or less, or 0.1(%) or less may be present in addition to the main peak for 1,2-dichlorobenzene (ODCB). The area (%) is related to the purity of the second organic solvent. The peak having the above area (%) may be a peak accountable for the aromatic compound containing 3 or more of chlorine (Cl). As the area (%) of the aromatic compound containing 3 or more of chlorine (Cl) is smaller, a second organic solvent of high purity can be obtained.

In addition, according to an embodiment of the present invention, when the second organic solvent is measured by gas chromatography (GC), the main peak for 1,2-dichlorobenzene (ODCB), which is the second organic solvent, may appear, and the peak accountable for the aromatic compound containing 3 or more of chlorine (Cl) may appear within 2 minutes in an area exceeding 0.5(%). In such event, the organic solvent is to be purified to adjust the area (%) to 0.5(%) or less, 0.3(%) or less, or 0.1(%) or less.

In addition, according to an embodiment, when the diisocyanate composition is prepared, the total content of cations in the second organic solvent is adjusted to a specific range to suppress side reactions caused by the cations remaining in the diisocyanate composition prepared therefrom, whereby it is possible to enhance the yield and purity of the diisocyanate composition and to enhance the transmittance while preventing the occurrence of yellowing, striae, and cloudiness when applied to an optical material.

Specifically, the total content of cations in the second organic solvent may be 1.5 ppm to 4.9 ppm, 1.5 ppm to 4.8 ppm, 1.5 ppm to 4.7 ppm, 1.5 ppm to 4.5 ppm, 2 ppm to 4.8 ppm, 2 ppm to 4.5 ppm, 3 ppm to 4.8 ppm, 3 ppm to 4.5 ppm, or 4 ppm to 5 ppm.

If the total content of cations in the second organic solvent falls outside the above range, the content of cations remaining in the diisocyanate composition prepared therefrom may be increased, and side reactions by the remaining cations may be promoted, whereby the physical properties of the final optical lens may be deteriorated. Specifically, if the total content of cations in the second organic solvent exceeds 5 ppm, the yield and purity of the diisocyanate composition may be deteriorated, striae may occur when an optical material is prepared since the reactivity is increased, and the optical characteristics such as transmittance and yellow index may be deteriorated.

The cations in the second organic solvent according to an embodiment of the present invention may comprise a monovalent cation.

The monovalent cation may comprise at least one selected from the group consisting of $Na^+$, $K^+$, and $N_4^+$.

According to an embodiment of the present invention, in order to adjust the content of cations in the second organic solvent used in the preparation of a diisocyanate composition, the amounts of $Na^+$, $K^+$, and $NH_4^+$ may be controlled, and their respective contents are as follows.

The content of $Na^+$ may be 0.8 ppm to 4.8 ppm. Specifically, the content of $Na^+$ may be 1 ppm to 4.5 ppm, 2 ppm to 4.5 ppm, 3 ppm to 4.5 ppm, 3 ppm to 4.2 ppm, or 3.6 ppm to 4.2 ppm.

The content of $K^+$ may be 0.1 ppm to 1 ppm. Specifically, the content of $K^+$ may be 0.1 ppm to 0.8 ppm, 0.1 ppm to 0.6 ppm, 0.1 ppm to 0.5 ppm, or 0.2 ppm to 0.5 ppm.

The content of $NH_4^+$ may be 0.1 ppm to 1 ppm. Specifically, the content of $NH_4^+$ may be 0.1 ppm to 0.8 ppm, 0.1 ppm to 0.6 ppm, 0.1 ppm to 0.5 ppm, or 0.2 ppm to 0.5 ppm.

In addition, the weight ratio of $Na^+$ and $K^+$ may be 1:0.02 to 0.2, 1:0.02 to 0.15, 1:0.02 to 0.1, or 1:0.05 to 0.1.

In addition, the weight ratio of $Na^+$ and $NH_4^+$ may be 1:0.02 to 0.2, 1:0.02 to 0.15, 1:0.02 to 0.1, or 1:0.05 to 0.1.

In addition, the weight ratio of $K^+$ and $NH_4^+$ may be 1:0.5 to 1.5, 1:0.7 to 1.2, or 1:0.8 to 1.2.

The total content of cations and the respective contents of $Na^+$, $K^+$, and $NH_4^+$ are the contents in the second organic solvent introduced in the preparation of the diisocyanate composition according to the embodiment of the present invention. These contents may be adjusted in advance before the second organic solvent is introduced to the reaction.

In order to adjust the total content of cations contained in the second organic solvent to the above range, the process may further comprise measuring the content of cations in the second organic solvent before the diamine hydrochloride composition is reacted with triphosgene.

The total content of cations in the second organic solvent may be measured by, for example, ion chromatography (IC). For example, it may be measured using a Metrohm 882 Compact IC Plus.

As a result of the measurement, if the total content of cations in the second organic solvent exceeds 5 ppm, the second organic solvent may be purified to adjust the total content of cations to the above range. The second organic solvent containing cations whose content has been adjusted as described above may be used in the reaction.

In addition, as a result of the measurement, if the total content of cations in the second organic solvent is 1 ppm to 5 ppm, the second organic solvent, as it is, may be introduced into the reaction without purification thereof.

The total content of cations in the second organic solvent before purification is not particularly limited as long as the content of cations in the organic solvent after purification can be adjusted in an amount of 1 ppm to 5 ppm. For example, it may be 1 ppm to 10 ppm, 1 ppm to 9 ppm, 2 ppm to 8 ppm, or 3 ppm to 7.5 ppm.

The content of $Na^+$ in the second organic solvent before purification may be adjusted to 0.8 ppm to 10 ppm. Specifically, the content of $Na^+$ in the second organic solvent before purification may be 0.8 ppm to 9 ppm, 1 ppm to 8 ppm, 2 ppm to 8 ppm, 3 ppm to 7 ppm, or 3 ppm to 6.5 ppm.

The content of $K^+$ in the second organic solvent before purification may be 0.1 ppm to 1 ppm. Specifically, the content of $K^+$ in the second organic solvent before purification may be 0.1 ppm to 0.8 ppm, 0.1 ppm to 0.7 ppm, or 0.2 ppm to 0.6 ppm.

The content of $NH_4^+$ in the second organic solvent before purification may be 0.1 ppm to 1 ppm. Specifically, the content of $NH_4^+$ in the second organic solvent before purification may be 0.1 ppm to 0.8 ppm, 0.1 ppm to 0.7 ppm, or 0.2 ppm to 0.6 ppm.

The yield of the second organic solvent after distillation purification may be 85% or more, 87% or more, 88% or more, 90% or more, or 92% or more.

Meanwhile, the following Reaction Scheme 2 shows an example of the reaction in this step.

[Reaction Scheme 2]

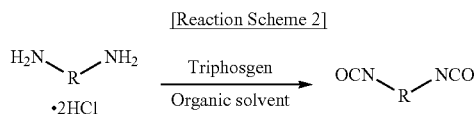

In the above scheme, R comprises an aromatic ring, an aliphatic ring, an aliphatic chain, and the like. As a specific example, R may be xylylene, norbornene, hydrogenated xylylene, isophorone, or hexamethylene, but it is not limited thereto.

Specifically, the diamine hydrochloride composition prepared above is introduced to a second organic solvent, reacted with triphosgene (BTMC, bis(trichloromethyl)carbonate), and then purified to obtain a diisocyanate composition.

The amount (weight) of the second organic solvent introduced may be 1 to 5 times the weight of the diamine hydrochloride composition. If the introduced amount is within the above range, it is possible to prevent the use of excessive organic solvents while the yield of the final diisocyanate is high. Specifically, the second organic solvent may be introduced to the reaction in an amount of 2 to 5 times, or 3 to 5 times, the weight of the diamine hydrochloride composition.

The reaction temperature of the diamine hydrochloride composition and triphosgene may be 110° C. to 160° C. The reaction temperature of the diamine hydrochloride composition and triphosgene is 110° C. or higher or 115° C. or higher, so that the reaction between the diamine hydrochloride and triphosgene is carried out more smoothly, which may be advantageous for increasing the yield and shortening the reaction time. In addition, if the reaction temperature of the diamine hydrochloride composition and triphosgene is 160° C. or less, it is possible to suppress the generation of impurities such as tar when the final diisocyanate is produced. For example, the reaction temperature of the diamine hydrochloride composition and triphosgene may be 115° C. to 160° C., 115° C. to 140° C., 115° C. to 130° C., 130° C. to 160° C., or 120° C. to 150° C.

In addition, if the reaction temperature of the diamine hydrochloride composition and triphosgene is 130° C. or lower, it may be more advantageous for suppressing impurities containing chlorine (e.g., chloromethylbenzyl isocyanate, 1,3-bis(chloromethyl)benzene, and the like). Specifically, the reaction temperature of the diamine hydrochloride composition and triphosgene may be 115° C. to 130° C. More specifically, the reaction temperature of the diamine hydrochloride composition and triphosgene may be 115° C. to 120° C.

The reaction of the diamine hydrochloride composition with triphosgene may be carried out for 5 hours to 100 hours. If the reaction time is within the above range, the reaction time is not excessive, and the production of unreacted materials due to the generation of phosgene can be minimized. Specifically, the reaction of the diamine hydrochloride composition with triphosgene may be carried out for 15 hours to 40 hours, 20 hours to 35 hours, or 24 hours to 30 hours.

As a specific example, the reaction of the diamine hydrochloride composition with triphosgene may be carried out at a temperature of 115° C. to 160° C. for 5 hours to 100 hours.

The diamine hydrochloride composition and triphosgene may be introduced to the reaction at an equivalent ratio of 1:1 to 5. When the equivalent ratio is within the above range, the reaction efficiency is high, and it is possible to prevent an increase in the reaction time due to an excessive introduction. Specifically, the diamine hydrochloride composition and triphosgene may be introduced to the reaction at an equivalent ratio of 1:1.5 to 4 or 1:2 to 2.5.

The reaction of the diamine hydrochloride composition and triphosgene may sequentially comprise mixing the diamine hydrochloride composition with the second organic solvent to obtain a first solution; mixing triphosgene with the second organic solvent to obtain a second solution; and introducing the second solution to the first solution and stirring them.

In such event, the introduction of the second solution and stirring may be carried out at a temperature of 110° C. to 160° C. In addition, the introduction of the second solution may be divided into two or more times for a total of 25 hours to 40 hours. In addition, here, the time for each introduction may be 5 hours to 25 hours or 10 hours to 14 hours. In addition, the time for further reaction by stirring after the introduction may be 2 hours to 5 hours or 3 hours to 4 hours.

Alternatively, the reaction of the diamine hydrochloride composition and triphosgene may sequentially comprise (2a) introducing the second organic solvent to a second reactor; (2b) introducing the diamine hydrochloride composition to the second reactor and stirring them; and (2c) introducing triphosgene to the second reactor and stirring them.

In such event, the introduction of triphosgene in step (2c) may be carried out by introducing a solution in which triphosgene is dissolved in the same solvent as the second organic solvent to the reactor as divided into two or more times at a temperature of 110° C. to 130° C. or 115° C. to 130° C. for a total of 25 hours to 40 hours. In such event, the time for each introduction of triphosgene may be 5 hours to 25 hours or 10 hours to 14 hours. In addition, the time for further reaction by stirring after the introduction may be 2 hours to 5 hours or 3 hours to 4 hours.

Upon the reaction, the reaction resultant may be cooled at 90° C. to 110° C.

The resultant obtained through the reaction may be further subjected to separation, degassing, cooling, filtration, distillation, and the like.

For example, after the reaction, the reaction resultant may be subjected to degassing at 80° C. to 150° C. with the bubbling of nitrogen gas. In addition, after the degassing, it may be cooled to 10° C. to 30° C., and solids may be filtered off.

The diisocyanate composition may be obtained by distillation after the reaction of the diamine hydrochloride composition and triphosgene.

The distillation may comprise distillation to remove the second organic solvent. For example, after the reaction, the reaction resultant may be distilled at 40° C. to 60° C. for 2 hours to 8 hours to remove the second organic solvent. The pressure during the distillation may be 2.0 torr or less, 1.0 torr or less, 0.5 torr or less, or 0.1 torr or less. In addition, the second organic solvent may be recovered and recycled through the distillation.

In addition, the distillation may comprise distilling the diisocyanate. For example, the distillation may comprise distillation of a diisocyanate at 100° C. to 130° C. If the distillation temperature is within the above range, it is more advantageous for preventing a deterioration in the physical properties of the final optical lens such as stria, cloudiness, and yellowing by effectively removing hydrolyzable chlorine compounds generated at high temperatures such as chloromethylbenzyl isocyanate (CBI) and 1,3-bis(chloromethyl)benzene. Specifically, the distillation may be carried out by setting the bottom temperature of the distiller to 100° C. to 130° C. For example, the distillation may be carried out by setting the reboiler temperature to 100° C. to 130° C.

In addition, the pressure during the distillation may be 2.0 torr or less, 1.0 torr or less, 0.5 torr or less, or 0.1 torr or less. Specifically, the distillation may comprise distillation of a diisocyanate at a temperature of 100° C. to 130° C. and a pressure of 2 torr or less.

In addition, the time for distillation of a diisocyanate may be 1 hour or longer, 2 hours or longer, or 3 hours or longer, and may be 10 hours or shorter or 5 hours or shorter. Specifically, the distillation of a diisocyanate may be carried out for 2 hours to 10 hours.

The yield of the distillation of a diisocyanate may be 80% or more, specifically 85% or more, or 90% or more. In such event, the distillation yield may be calculated by measuring the amount of the diisocyanate composition upon the distillation relative to the theoretical amount of the diisocyanate composition produced from the amounts of the diamine hydrochloride composition introduced to the reaction with triphosgene.

According to the process of the above embodiment, the reaction temperature range of the diamine hydrochloride composition and triphosgene is controlled, whereby the crude diisocyanate composition before purification may contain very little impurities. Specifically, the diisocyanate composition may contain 99.0% by weight or more of the diisocyanate before the distillation of a diisocyanate. In addition, the diisocyanate composition may contain 99.9% by weight or more of the diisocyanate after the distillation of a diisocyanate.

In addition, the content of aromatic compounds having a halogen group in the diisocyanate composition may be 1,000 ppm or less.

In addition, the yield of the diisocyanate composition finally obtained may be 80% or more, 85% or more, or 90% or more.

In addition, the process may further comprise secondarily distilling the reaction resultant obtained by reacting the diamine hydrochloride composition and triphosgene.

The secondary distillation may comprise first distillation and second distillation.

For example, the step of obtaining the diisocyanate composition further comprises secondarily distilling a reaction resultant obtained by reacting the diamine hydrochloride composition, specifically the treated diamine hydrochloride composition, and triphosgene. The secondary distillation may comprise a process of distilling the reaction resultant at 40° C. to 150° C. for 2 hours to 20 hours. Specifically, it may comprise first distillation at 40° C. to 60° C. for 2 hours to 8 hours and second distillation at 100° C. to 120° C. for 2 hours to 10 hours. The first distillation and/or the second distillation may be carried out at 0.5 Torr or less.

The organic solvent may be recovered and recycled through the first distillation, and a final diisocyanate may be obtained through the second distillation.

In addition, the purity of the (crude) diisocyanate composition before the secondary distillation may be 90% or more, 95% or more, 99% or more, or 99.1% or more.

According to the process of the above embodiment, the yield and purity of the diisocyanate composition thus prepared are high, an optical material of high quality can be obtained using the same, the recycling rate of organic solvents is excellent, it is environmentally friendly since highly toxic phosgene gas is not used, it is possible to react at atmospheric pressure, and a separate apparatus for pressurization or rapid cooling is not required.

Adjustment of the Content of Water in Triphosgene

The content of water in triphosgene used in the reaction of the diamine hydrochloride composition and triphosgene may be adjusted in advance. For example, the content of water in triphosgene used in the reaction of the diamine hydrochloride composition and triphosgene may be 200 ppm or less.

The content of water in the triphosgene may be adjusted in advance before it is introduced to the reaction. Thus, the process may further comprise measuring the content of water in the triphosgene before it is introduced to the reaction.

As a result of the measurement, if the content of water in triphosgene is 200 ppm or less, it may be introduced to the reaction as it is. However, if the content of water in the triphosgene exceeds 200 ppm, the content of water may be adjusted.

For example, the content of water in the triphosgene may be adjusted through at least one further step of washing and drying.

As an example, the triphosgene may be washed with a solvent having a polarity index of 3.9 to 5.7 before it is introduced to the reaction in step (2). If the solvent used for washing as described above has a polarity index of 3.9 or more, it is miscible with water and effective in removing water. In addition, if it has a polarity index of 5.7 or less, it does not dissolve triphosgene, thereby increasing the yield.

In addition, if the solvent used in the washing does not have a hydroxyl group or an amine group, it is possible to enhance the purity and yield of the product by preventing side reactions with triphosgene.

In addition, if the solvent used for washing has a boiling point of 85° C. or lower, it reduces the residual solvents after drying, thereby enhancing the purity and yield of the product. For example, the boiling point of the solvent used for washing may be 30° C. to 85° C.

Specifically, the solvent used for washing may include at least one selected from the group consisting of tetrahydrofuran (THF), ethyl acetate, methyl acetate, methyl ethyl ketone, and acetone. More specifically, the solvent used for washing may include at least one selected from tetrahydrofuran and acetone.

In addition, the content of water in the triphosgene may be adjusted by drying it under a reduced pressure. For example, the triphosgene may be dried for 2 hours to 10 hours under the conditions of a temperature of 20° C. to 60° C. and a pressure of 0.01 torr to 100 torr before it is introduced to the reaction.

The drying step may be performed after the above washing is first performed. That is, the triphosgene, after the washing, may be further dried under the conditions of a temperature of 20° C. to 60° C. and a pressure of 0.01 torr to 100 torr.

In the triphosgene, after the drying, the content of the residual solvents used in the washing may be less than 100 ppm.

In addition, the content of water in the triphosgene may be 100 ppm or less, or 50 ppm or less, after the further step (i.e., at least one of washing and drying).

As described above, the content of water in triphosgene is adjusted within a specific range, so that the formation of urea during the phosgenation reaction can be suppressed, thereby preventing a deterioration in the physical properties of the final optical lens such as stria, cloudiness, and yellowing.

Adjustment of the Content of Water in the Second Organic Solvent

According to the above embodiment, the content of water in the organic solvent (i.e., second organic solvent) used in the reaction of the diamine hydrochloride composition and triphosgene is 200 ppm or less.

The content of water in the second organic solvent may be adjusted in advance before it is introduced to the reaction. Thus, the process may further comprise measuring the content of water in the second organic solvent before it is introduced to the reaction.

As a result of the measurement, if the content of water in the second organic solvent is 200 ppm or less, it may be introduced to the reaction as it is. However, if the content of water in the second organic solvent exceeds 200 ppm, the content of water may be adjusted.

Specifically, the content of water in the second organic solvent may be adjusted by dehydration under a reduced pressure. The pressure during the dehydration may be 2.0 torr or less, 1.0 torr or less, 0.5 torr or less, or 0.1 torr or less. The temperature during the dehydration is 20° C. or higher, which is advantageous for removing sufficient water. In addition, it is 40° C. or lower, which is advantageous for increasing the dehydration yield by suppressing the evaporation of the solvent during the dehydration step. Thus, the temperature during the dehydration may be adjusted to 20° C. to 40° C. In addition, the time for the dehydration may be 1 hour or longer or 2 hours or longer, and 5 hours or shorter or 3 hours or shorter. As a specific example, the dehydration may be performed for 1 hour to 3 hours under a pressure of 0.5 torr or less. The equipment and method used for the dehydration are not particularly limited. For example, the dehydration may be performed with a vacuum pump with stirring.

The dehydration yield may be 80% or more, specifically 85% or more, or 90% or more.

In addition, the content of water in the second organic solvent may be 100 ppm or less after the dehydration.

As described above, the content of water in the organic solvent used in the reaction of a diamine hydrochloride composition and triphosgene is adjusted within a specific range, so that the formation of urea during the phosgenation reaction can be suppressed, thereby preventing a deterioration in the physical properties of the final optical lens such as stria, cloudiness, and yellowing. In addition, the content of water contained in the organic solvent during the reaction, transport, and storage is reduced. Even if the organic solvent is recovered after the reaction and then recycled for the next reaction, the quality of the product may not be deteriorated.

Diisocyanate Composition

The present invention may provide a diisocyanate composition obtained by the above preparation process. The diisocyanate composition prepared using a diamine hydrochloride composition and triphosgene as described above may be improved in terms of the color and haze.

The diisocyanate composition may have an APHA (American Public Health Association) color value of 20 or less or 10 or less. Specifically, the diisocyanate composition may have an APHA color value of 1 to 20 or 1 to 10.

In addition, the diisocyanate composition is a composition comprising a diisocyanate wherein the total content of cations in the composition may be 100 ppm or less.

According to the above embodiment, a diisocyanate composition is prepared using an organic solvent in which the total content of cations is adjusted. As a result, the content of cations in the diisocyanate composition may be adjusted to the above range as well.

Specifically, the total content of cations in the composition may be 90 ppm or less, 80 ppm or less, 1 ppm to 80 ppm, 1 ppm to 75 ppm, 10 ppm to 75 ppm, or 10 ppm to 50 ppm.

The cations contained in the diisocyanate composition may promote side reactions, resulting in a deterioration in the physical properties of the final optical lens as striae occur. For example, if the total content of cations in the composition exceeds 100 ppm, the yield and purity of the diisocyanate composition may be deteriorated, striae may occur when an optical material is prepared since the reactivity is increased, and the optical characteristics such as transmittance and yellow index may be deteriorated.

The cations may be derived from the cations contained in the organic solvent used in the preparation of the diisocyanate composition or may be generated through various routes during the reaction process.

Specifically, the cations in the diisocyanate composition may comprise monovalent to trivalent cations. Specifically, the cations in the diisocyanate composition may comprise at least one selected from the group consisting of $Na^+$, $K^+$, and $N_4^+$.

In addition, the cations in the diisocyanate composition may comprise an ion of at least one metal selected from the group consisting of Fe, Ca, Mg, Cr, Mn, Ni, Cu, and Zn in addition to the above monovalent cations.

In addition, the diisocyanate composition may have a haze of 10% or less, 5% or less, or 3% or less.

In addition, the content of a diisocyanate in the diisocyanate composition may be 90% by weight or more, 95% by weight or more, or 99.5% by weight or more, specifically 90% by weight to less than 100% by weight, more specifically 99% by weight to less than 100% by weight.

In addition, the diisocyanate composition may further comprise benzyl isocyanate, methylbenzyl isocyanate, cyanobenzyl isocyanate, and the like. The total content of these components may be about 1% by weight or less.

The diisocyanate composition may comprise xylylene diisocyanate or other diisocyanates used in the preparation of optical lenses. Specifically, it may comprise at least one selected from the group consisting of orthoxylylene diisocyanate (o-XDI), metaxylylene diisocyanate (m-XDI), paraxylylene diisocyanate (p-XDI), norbornene diisocyanate (NBDI), hydrogenated xylylene diisocyanate (H6XDI), isophorone diisocyanate (IPDI), and hexamethylene diisocyanate (HDI). More specifically, the diisocyanate may comprise m-xylylene diisocyanate (m-XDI), p-xylylene diisocyanate (p-XDI), or a mixture thereof.

The diisocyanate composition according to an embodiment may comprise m-xylylene diisocyanate (m-XDI) in an amount of 99% by weight to less than 100% by weight, for example, 99.5% by weight to less than 100% by weight or 99.7% by weight to less than 100% by weight.

If m-xylylene diisocyanate is contained in the composition in an amount less than the above range, not only the optical characteristics (especially, striae, transmittance, and the like) but also the mechanical properties (such as impact resistance, tensile strength, and the like) of the final product may be impaired due to the nonuniformity in the polymerization reactivity of the composition and in the chemical structure of the cured product. Further, yellowing may occur depending on other components incorporated therein.

In addition, p-xylylene diisocyanate may be contained in an amount of greater than 0% by weight to 0.5% by weight, greater than 0% by weight to 0.3% by weight, greater than 0% by weight to 0.15% by weight, greater than 0% by weight to 0.1% by weight, greater than 0% by weight to 0.05% by weight, greater than 0% by weight to 0.03% by weight, or greater than 0% by weight to 0.01% by weight, based on the total weight of the composition.

If p-xylylene diisocyanate is contained in the composition in an amount exceeding the above content range, the optical characteristics may be impaired as striae occur or the transmittance is lowered due to the nonuniform polymerization caused by differences in the reactivity or due to the crystallization caused by changes in the chemical structure of the polymer.

In addition, the diisocyanate composition of the present invention may further comprise at least one selected from the group consisting of a benzyl isocyanate having a methyl group and cyanobenzyl isocyanate.

The at least one selected from the group consisting of a benzyl isocyanate having a methyl group and cyanobenzyl isocyanate may be employed in an amount of, for example, 0.5% by weight or less, 0.3% by weight or less, 0.1% by weight or less, 0.05% by weight or less, 0.02% by weight or less, or 0.01% by weight or less.

If the at least one selected from the group consisting of a benzyl isocyanate having a methyl group and cyanobenzyl isocyanate is employed in the composition in an amount exceeding the above content range, it affects the chemical structure of the polymer, resulting in a deterioration in the mechanical properties or the thermal resistant characteristics such as glass transition temperature of the final product. Further, due to the influence of the cyano groups, yellowing may occur at the time of thermal curing for producing a lens or after the production of the lens depending on the external environment, thereby causing serious damage to the long-term reliability of the lens.

The purity (purity after distillation) of the diisocyanate composition may be 95% or more, 99% or more, 99.5% or more, or 99.9% or more.

In addition, the yield (yield after distillation) of the diisocyanate composition may be 90% or more, 91% or more, or 92% or more.

In addition, if the diisocyanate composition has a content of cations within the above range, the reactivity (or polymerization rate) of a polymerizable composition using the same may be appropriate. Specifically, the polymerizable composition using the diisocyanate composition may have a rate of change in viscosity over time according to the following Equation 1, that is, a b value of 0.1 to 0.3, specifically 0.13 to 0.28, 0.13 to 0.25, or 0.15 to 0.23.

$$Y = a \times \exp(b \times X) \quad \text{[Equation 1]}$$

In the above equation, Y is the viscosity (cPs) of the polymerizable composition, X is the time (hr) elapsed after the preparation of the polymerizable composition, for example, a variable from 5 to 24, and a is a constant, which refers to the initial viscosity (cPs), may be determined between, for example, 20 and 1,000 depending on the polymerization conditions, and does not affect the determination of the b value.

In the diisocyanate composition obtained by the preparation process according to the embodiment of the present invention, it is possible to achieve appropriate reactivity (or polymerization rate) when an optical material is prepared and to improve the optical properties by preventing the occurrence of yellowing and striae and enhancing the transmittance.

In the diisocyanate composition obtained by the preparation process according to the embodiment of the present invention, it is possible to improve the optical properties by preventing the occurrence of yellowing, striae, and cloudiness and enhancing the transmittance.

In addition, according to the process of the above embodiment, the yield of diisocyanate is high, the recycling rate of organic solvents is excellent, it is environmentally friendly since highly toxic phosgene gas is not used, it is possible to react at atmospheric pressure, and a separate apparatus for pressurization or rapid cooling is not required.

Measurement of the Color and Transparency of a Reaction Solution

The step of obtaining a diisocyanate composition from the diamine hydrochloride composition and triphosgene may comprise (aa) reacting the diamine hydrochloride composition with triphosgene in a second organic solvent in a reactor to obtain a reaction solution; (ab) measuring the color and transparency of the reaction solution; and (ac) obtaining a diisocyanate composition from the reaction solution.

In the reaction of the diamine hydrochloride composition and triphosgene, the color and transparency of the reaction solution may be measured to adjust the reaction conditions.

For example, in the reaction of metaxylylenediamine hydrochloride and triphosgene to obtain metaxylylene diisocyanate, the reaction solution at the beginning of the reaction may be opaque colorless or white, and the reaction solution at the time when the reaction is ordinarily completed may be transparent or close to transparent in a light brown color.

For example, in the step of measuring the color and transparency of the reaction solution, the reaction solution may have a transparent light brown color.

Specifically, the reaction solution may have an $L^*$ value of 45 to 60, an $a^*$ value of 3 to 15, and a $b^*$ value of 15 to 30 in the CIE-LAB color coordinate. More specifically, the reaction solution may have an $L^*$ value of 50 to 55, an $a^*$ value of 5 to 10, and a $b^*$ value of 20 to 25 in the CIE-LAB color coordinate.

In addition, the reaction solution may have a transmittance of 60% or more, 70% or more, 80% or more, or 90% or more, for light having a wavelength of 550 nm. In addition, the reaction solution may have a haze of 20% or less, 10% or less, 5% or less, or 3% or less. Specifically, the reaction solution may have a transmittance of 70% or more for light having a wavelength of 550 nm and a haze of 10% or less. More specifically, the reaction solution may have a transmittance of 80% or more for light having a wavelength of 550 nm and a haze of 5% or less.

On the other hand, if the reaction of the metaxylylenediamine hydrochloride and triphosgene is not completed, the reaction solution may be opaque or have a precipitate, and the color may be pale, white, or colorless. In addition, if side reactions take place to a significant extent, the reaction solution may be opaque or may have a color other than light brown, for example, a dark brown or dark color.

The reaction of the diamine hydrochloride composition and triphosgene may be carried out simultaneously with the step of measuring the color and transparency of the reaction solution.

That is, while the reaction of the diamine hydrochloride composition and triphosgene is being carried out, the color and transparency of the reaction solution may be measured in real time.

In addition, for more accurate measurement, a part of the reaction solution may be collected to precisely measure the color and transparency thereof. For example, the measurement of the color and transparency of the reaction solution may be carried out by collecting a part of the reaction solution and measuring the color and transparency of the collected reaction solution.

In such event, the reaction equivalent, reaction temperature, or reaction time may be adjusted according to the color and transparency of the reaction solution. For example, the timing for terminating the reaction may be determined according to the color and transparency of the reaction solution. Specifically, the timing for terminating the reaction may come after when the reaction solution turns a transparent light brown color.

As an example, the reactor may have a viewing window, and the measurement of the color and transparency of the reaction solution may be carried out through the viewing window.

The reactor is connected to one or more stages of condensers. Once the gas generated in the reactor has been transferred to the one or more stages of condensers, the second organic solvent present in the gas may be condensed and recycled to the reactor.

The one or more stages of condensers are connected to a first scrubber and a second scrubber. The gas transferred from the reactor to the one or more stages of condensers contains hydrogen chloride gas and phosgene gas, the first scrubber may dissolve the hydrogen chloride gas in water to produce an aqueous solution, and the second scrubber may neutralize the phosgene gas with an aqueous NaOH solution.

In addition, the reactor is connected to one or more stages of distillers. The reaction solution is transferred to the one or more stages of distillers, and the one or more stages of distillers may separate the diisocyanate composition and the second organic solvent from the reaction solution.

The separated second organic solvent may be recycled for the reaction of the diamine hydrochloride composition and triphosgene.

FIG. 2 shows an example of the process equipment for the reaction of a diamine hydrochloride composition and triphosgene.

First, a first tank (T-1) is charged with a second organic solvent and triphosgene, and the temperature is maintained to be constant by refluxing hot water. The inside of a reactor (R-1) is purged with nitrogen, a second organic solvent is introduced thereto with stirring, a diamine hydrochloride composition is slowly introduced thereto, and they are stirred while the internal temperature of the reactor is maintained to be constant.

Thereafter, triphosgene in the second organic solvent is gradually introduced into the reactor (R-1) from the first tank (T-1). The introduction of triphosgene in the second organic solvent is carried out at a time or divided into two or more times. At that time, stirring is performed while the internal temperature of the reactor (R-1) is maintained to be constant. Upon completion of the introduction, an additional reaction is carried out while stirring is performed for a certain period of time. As an example, the color and transparency of the reaction solution are monitored with the naked eyes through a viewing window (G-1) provided in the reactor (R-1). As another example, the color and transparency of the reaction solution are measured with an optical device through the viewing window (G-1) provided in the reactor (R-1). The optical device may include a digital camera, a spectrometer, and optical analysis equipment.

The gas (second organic solvent, hydrogen chloride, phosgene, and the like) present inside the reactor (R-1) is transferred to a first condenser (C-1). In the first condenser (C-1), the second organic solvent is firstly condensed by cooling and recycled to the reactor (R-1), and the remaining gas is transferred to a second condenser (C-2). In the second condenser (C-2), the second organic solvent is secondly condensed by cooling and recycled to the reactor (R-1), and the remaining gas is transferred to a third condenser (C-3). In the third condenser (C-3), the second organic solvent is thirdly condensed by cooling and recycled to the reactor (R-1).

Once the second organic solvent is removed while it passes through the multi-stage condensers as described above, the remaining gas (hydrogen chloride, phosgene, and the like) is transferred to a first scrubber (S-1). In the first scrubber (S-1), hydrogen chloride gas is dissolved in water to obtain an aqueous hydrochloric acid solution and stored in a second tank (T-2), and the remaining gas is transferred to a second scrubber (S-2). In the second scrubber (S-1), phosgene ($COCl_2$) gas may be neutralized with an aqueous sodium hydroxide solution stored in a third tank (T-3) and removed.

The reaction solution obtained from the reactor (R-1) is sequentially transferred to a first distiller (D-1) and a second distiller (D-2). While it undergoes first and second distillation, the diisocyanate composition and the second organic solvent are separated from the reaction solution.

The second organic solvent separated from the reaction solution may be transferred to, and stored in, a solvent recovery apparatus (V-1). Thereafter, it may be recycled for the reaction of the diamine hydrochloride composition and triphosgene.

In addition, the diisocyanate composition separated from the reaction solution may be further subjected to filtration and drying to provide a final product.

[Process for Preparation of an Optical Lens]

The diisocyanate composition prepared in the above embodiment may be combined with other components to prepare a composition for an optical material. That is, the composition for an optical material comprises a diisocyanate composition prepared according to the above embodiment and a thiol or an episulfide. The composition for an optical material may be used to prepare an optical material, specifically an optical lens. For example, the composition for an optical material is mixed and heated and cured in a mold to produce an optical lens. The process for preparing an optical lens or the characteristic thereof described below should be understood as a process for preparing various optical materials or the characteristic thereof that can be implemented using the diisocyanate composition according to the embodiment in addition to an optical lens.

The process for preparing an optical lens according to an embodiment comprises reacting a diamine with an aqueous hydrochloric acid solution to obtain a diamine hydrochloride composition; reacting the diamine hydrochloride composition with triphosgene in a second organic solvent to obtain a diisocyanate composition, and mixing the diisocyanate composition with a thiol or an episulfide and polymerizing and curing the resultant in a mold, wherein the content of water, the content of cations, or the content of an aromatic compound containing 3 or more of chlorine (Cl) in the second organic solvent is adjusted.

Specifically, the content of water in the organic solvent may be 200 ppm or less, the organic solvent may comprise an aromatic compound containing 3 or more of chlorine (Cl) in an amount of 5,000 ppm or less, and the total content of cations in the organic solvent may be adjusted to 1 ppm to 5 ppm.

In addition, the diamine is xylylenediamine, and the diisocyanate composition may comprise xylylene diisocyanate.

The thiol may be a polythiol containing two or more SH groups. It may have an aliphatic, alicyclic, or aromatic skeleton. The episulfide may have two or more thioepoxy groups. It may have an aliphatic, alicyclic, or aromatic skeleton.

Specific examples of the thiol include bis(2-mercaptoethyl) sulfide, 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, tetrakis(mercaptomethyl)methane, 2-(2-mercaptoethylthio)propane-1,3-dithiol, 2-(2,3-bis(2-mercaptoethylthio)propylthio)ethanethiol, bis(2,3-dimercaptopropanyl)sulfide, bis(2,3-dimercaptopropanyl) disulfide, 1,2-bis(2-mercapto-ethylthio)-3-mercaptopropane, 1,2-bis(2-(2-mercaptoethylthio)-3-mercaptopropylthio)ethane, bis(2-(2-mercaptoethylthio)-3-mercaptopropyl)sulfide, bis(2-(2-mercaptoethylthio)-3-mercaptopropyl)disulfide, 2-(2-mercaptoethylthio)-3-2-mercapto-3-[3-mercapto-2-(2-mercaptoethylthio)-propylthio]propylthio-propane-1-thiol, 2,2-bis-(3-mercapto-propionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R,11S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio)propyl)thio)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), trimethylolpropane tris(3-mercaptopropionate), pentaethritol tetrakis(2-mercaptoacetate), bispentaerythritol-ether-hexakis(3-mercaptopropionate), 1,1,3,3-tetrakis(mercaptomethylthio)propane, 1,1,2,2-tetrakis(mercaptomethylthio)ethane, 4,6-bis(mercaptomethylthio)-1,3-dithiane, 2-(2,2-bis(mercaptodimethylthio)ethyl)-1,3-dithiane, 2,5-bismercaptomethyl-1,4-dithiane, bis(mercaptomethyl)-3,6,9-trithiaundecan-1,11-dithiol.

Preferably, the thiol may be 2-(2-mercaptoethylthio)propane-1,3-dithiol, 2,3-bis(2-mercaptoethylthio)propane-1-thiol, 2-(2,3-bis(2-mercaptoethylthio)propylthio)ethanethiol, 1,2-bis(2-mercaptoethylthio)-3-mercaptopropane, 1,2-bis(2-(2-mercaptoethylthio)-3-mercaptopropylthio)-ethane, bis(2-(2-mercaptoethylthio)-3-mercaptopropyl) sulfide, 2-(2-mercaptoethylthio)-3-2-mercapto-3-[3-mercapto-2-(2-mercaptoethylthio)]propylthio-propane-1-thiol, 2,2'-thiodiethanethiol, 4,14-bis(mercaptomethyl)-3,6,9,12,15-pentathiahectadecane-1,17-dithiol, 2-(2-mercaptoethylthio)-3-[4-(1-{4-[3-mercapto-2-(2-mercaptoethylthio)-propoxy]-phenyl}-1-methylethyl)-phenoxy]-propane-1-thiol, pentaerythritol tetrakis(3-mercaptopropionate), pentaerythritol mercaptoacetate, trimethanolpropanetrismercaptopropionate, glycerol trimercaptopropionate, dipentaerythritol hexamercaptopropionate, or 2,5-bismercaptomethyl-1,4-dithiane. The thiol may be any one or two or more of the exemplary compounds, but it is not limited thereto.

In addition, specific examples of the episulfide include bis(β-epithiopropylthio)methane, 1,2-bis(β-epithiopropylthio)ethane, 1,3-bis(β-epithiopropylthio)propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-β-epithiopropylthioethyl)thio]ethane, 1-(β-epithiopropylthio)-2-[[2-(2-β-epithiopropylthioethyl)thioethyl]thio]ethane, tetrakis(β-epithiopropylthiomethyl)methane, 1,1,1-tris(β-epithiopropylthiomethyl)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethy)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethyl)-5-[(2-β-epithiopropylthioethyl)thiomethyl]-3,7-ditianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthioethyl)thiomethyl]-3,6,9-trithiaundecane, 1,11-bis(β-epithiopropylthio)-4,7-bis(β-epithiopropylthiomethyl)-3,6,9-trithiaundecane, 1,3-bis(β-epithiopropylthio)cyclohexane, 1,4-bis(β-epithiopropylthio)cyclohexane, 1,3-bis(β-epithiopropylthiomethyl)cyclohexane, 1,4-bis(β-epithiopropylthiomethyl)cyclohexane, bis[4-(β-epithiopropylthio)cyclohexyl]methane, 2,2-bis[4-(β-epithiopropylthio)cyclohexyl]propane, bis[4-(β-epithiopropylthio)cyclohexyl] sulfide, 2,5-bis(β-epithiopropylthiomethyl)-1,4-dithiane, 2,5-bis(β-epithiopropylthioethylthiomethyl)-1,4-dithiane, 1,3-bis(β-epithiopropylthio)benzene, 1,4-bis(β-epithiopropylthio)benzene, 1,3-bis(β-epithiopropylthiomethyl)benzene, 1,4-bis(β-epithiopropylthiomethyl)benzene, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl] sulfone, and 4,4'-bis(β-epithiopropylthio)biphenyl.

The episulfide may be any one or two or more of the exemplary compounds, but it is not limited thereto. In addition, the episulfide may be a compound in which at least one of the hydrogens of its thioepoxy group is substituted with a methyl group.

The composition for an optical material may comprise the diisocyanate composition and the thiol or episulfide in a mixed state or in a separated state. That is, in the composition, they may be in a state of being compounded in contact with each other or separated from each other so as not to contact each other.

The composition for an optical material may comprise the thiol or episulfide and the diisocyanate composition at a weight ratio of 2:8 to 8:2, 3:7 to 7:3, or 4:6 to 6:4.

A catalyst, a chain extender, a crosslinking agent, an ultraviolet stabilizer, an antioxidant, an anti-coloring agent, a dye, a filler, a release agent, and the like may be further added depending on the purpose when the composition for an optical material and an optical lens are prepared.

The thiol or episulfide is mixed with a diisocyanate composition and other additives, which is defoamed, injected into a mold, and gradually polymerized while the temperature is gradually elevated from low to high temperatures. The resin is cured by heating to prepare an optical lens.

The polymerization temperature may be, for example, 20° C. to 150° C., particularly 25° C. to 120° C. In addition, a reaction catalyst, which is conventionally used in the production of polythiourethane, may be employed in order to control the reaction rate. Specific examples of the reaction catalyst are as exemplified above.

In addition, if required, the optical lens thus prepared may be subjected to physical or chemical treatment such as anti-reflection coating, hardness, enhancements in abrasion resistance and chemical resistance, anti-fogging, surface polishing, antistatic treatment, hard coat treatment, anti-reflection treatment, and dyeing treatment.

[Optical Material]

The optical material according to an embodiment of the present invention comprises a polythiourethane polymerized from a diisocyanate composition and a thiol or an episulfide, wherein the diisocyanate composition is obtained by reacting a diamine hydrochloride composition and triphosgene in a second organic solvent, and the organic solvent comprises water, cations, or an aromatic compound containing 3 or more of chlorine (Cl) in a specific amount.

Specifically, the content of water in the organic solvent may be 200 ppm or less, the organic solvent may comprise an aromatic compound containing 3 or more of chlorine (Cl) in an amount of 5,000 ppm or less, and the total content of cations in the organic solvent may be 1 ppm to 5 ppm.

The optical material prepared by the above process is an optical lens, which has excellent optical properties in terms of transparency, refractive index, and yellow index. For example, the optical lens may have a refractive index of 1.55 or more, specifically a refractive index of 1.55 to 1.77. Alternatively, the optical lens may have a refractive index of 1.6 or more, specifically a refractive index of 1.6 to 1.7. In addition, the optical lens may have an Abbe number of 30 to 50, specifically 30 to 45 or 31 to 40.

In addition, the optical lens may have a light transmittance of 80% or more, 85% or more, or 87% or more, which may be a total light transmittance. In addition, the optical lens may have a yellow index (Y.I.) of 30 or less, 25 or less, or 20 or less, for example, 1 to 25 or 10 to 20. Specifically, the optical lens may have a transmittance of 85% or more and a yellow index of 20 or less.

Accordingly, if an optical material is prepared using a diisocyanate composition prepared using an organic solvent in which water, cations, or an aromatic compound containing 3 or more of chlorine (Cl) is adjusted to a specific content according to an embodiment of the present invention, the optical characteristics are excellent since the transmittance can be enhanced and yellowing, striae, and cloudiness can be prevented. Thus, the diisocyanate composition and the process for preparing the same can be advantageously used to prepare high-quality eyeglass lenses, camera lenses, and the like.

MODE FOR CARRYING OUT THE INVENTION

Hereinafter, more specific embodiments are illustrated, but the present invention is not limited thereto.

Preparation Example: Adjustment of the Content of Water in an Organic Solvent

The content of water in 1,2-dichlorobenzene (ODCB), an organic solvent to be used in the reaction, was measured. If it was 200 ppm or less, the solvent, as it was, was used in the reaction. If it exceeded 200 ppm, the water content was adjusted to 200 ppm or less by dehydration. The dehydration was carried out by stirring with a vacuum pump of 0.5 torr or less under the conditions shown in Table 1 below.

The procedures for measuring the water content were as follows. First, the Karl Fischer reagent for the measurement of moisture was filled in a vaporized moisture meter (KEM, MKS-710S) installed in a glove box filled with dried nitrogen. The flow rate of nitrogen gas was 200 ml/minute, and the internal sublimation temperature was set to 120° C. Preliminary titration was performed to stabilize it until the draft value became 0.10 μg/s or less. Then, the moisture content was measured (back purge 30 minutes, cell purge 30 minutes, measurement time 40 minutes).

TABLE 1

| | Content of water in ODCB (ppm) | | Dehydration condition | | Dehydration yield (%) |
|---|---|---|---|---|---|
| | Before dehydration | After dehydration | Temp. (° C.) | Time (hr) | |
| Prep. Ex. A | 37 | 37 | — | — | 100% |
| Prep. Ex. B | 630 | 48 | 20 | 2 | 94% |
| Prep. Ex. C | 630 | 37 | 40 | 2 | 92% |
| Prep. Ex. D | 630 | 630 | — | — | 100% |
| Prep. Ex. E | 630 | 320 | 20 | 0.5 | 96% |
| Prep. Ex. F | 630 | 25 | 60 | 2 | 75% |
| Prep. Ex. G | 630 | 121 | 60 | 0.5 | 92% |

Examples 1-1 to 1-4

Step (1): Preparation of a Diamine Hydrochloride Composition

A reactor was charged with 1,009.4 g (9.46 moles) of an aqueous solution of 35% hydrochloric acid, followed by lowering the internal temperature of the reactor to 15° C. with stirring. While the temperature of the reactor was maintained at 20° C. to 50° C., 600.0 g (4.4 moles) of m-XDA was introduced for 1 hour. Upon completion of the introduction, the internal temperature of the reactor was lowered to 10° C., and it was stirred for 1 hour. Thereafter, 1,320.0 g of tetrahydrofuran (THF) was introduced, and the internal temperature of the reactor was lowered to −5° C., followed by stirring for 1 hour. Upon completion of the reaction, the diamine hydrochloride composition containing m-XDA-2HCl was separated by vacuum filtration using a filter, and the filtered tetrahydrofuran was recovered for reuse. The separated diamine hydrochloride composition was dried under vacuum at 90° C. and 0.5 torr to remove the residual solvent and water.

Step (2): Preparation of a Diisocyanate Composition

Reactor A was charged with 800 g of the diamine hydrochloride composition prepared above and 3,550 g of ODCB whose water content had been adjusted to 200 ppm or less, followed by heating them at about 125° C. with stirring. Reactor B was charged with 950 g of triphosgene (BTMC) and 800 g of ODCB whose water content had been adjusted to 200 ppm or less, which was stirred at about 60° C. for dissolution. While the temperature was maintained at 125° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas. Thereafter, it was cooled to 10° C., and the remaining solids were filtered using celite. The organic solvent (ODCB) was removed, and distillation was carried out to obtain a diisocyanate composition containing m-XDI. Here, the removal of the organic solvent was carried out for 8 hours at a pressure of 0.5 torr or less and a temperature of 60° C. In addition, the distillation was carried out for 10 hours at a temperature of 120° C. and a pressure of 0.5 torr or less.

Example 1-5

Step (1): Preparation of a Diamine Hydrochloride Composition

Reactor 1 was charged with 1,009.4 g (9.46 moles) of an aqueous solution of 35% hydrochloric acid, followed by lowering the internal temperature of the reactor to 15° C. with stirring. While the temperature of Reactor 1 was maintained at 50° C. or lower, 627.0 g (4.4 moles) of H6XDA was introduced for 1 hour. Upon completion of the introduction, the internal temperature of Reactor 1 was lowered to 10° C., and it was stirred for 1 hour. The internal temperature of Reactor 2 to which 2,640.0 g of diethyl ether had been charged was lowered to −5° C. The mixture in Reactor 1 was slowly added dropwise to Reactor 2 at 0° C. or lower. Upon completion of the addition, the diamine hydrochloride composition containing H6XDA·2HCl was separated by vacuum filtration using a filter, and the filtered diethyl ether was recovered for reuse. Thereafter, the separated diamine hydrochloride composition was dried under vacuum at 90° C. and 0.5 torr to remove the residual solvent and water.

Step (2): Preparation of a Diisocyanate Composition

Reactor A was charged with 823 g of the diamine hydrochloride composition prepared above and 3,550 g of ODCB (Preparation Example A) whose water content had been adjusted to 200 ppm or less, followed by heating them at about 125° C. with stirring. Reactor B was charged with 950 g of triphosgene (BTMC) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 3 hours to 4 hours. Upon completion of the reaction, nitrogen gas was blown into the solvent with bubbling at 125° C. to degas. Thereafter, it was cooled to 10° C., and the remaining solids were filtered using celite. The organic solvent (ODCB) was removed, and distillation was carried out to obtain a diisocyanate composition containing H6XDI. Here, the removal of the organic solvent was carried out for 8 hours at a pressure of 0.5 torr or less and a temperature of 60° C. In addition, the distillation was carried out for 10 hours at a temperature of 120° C. and a pressure of 0.5 torr or less.

Example 1-6

Step (1): Preparation of a Diamine Hydrochloride Composition

A reactor was charged with 1,009.4 g (9.46 moles) of an aqueous solution of 35% hydrochloric acid, followed by lowering the internal temperature of the reactor to 15° C. with stirring. While the temperature of the reactor was maintained at 50° C. or lower, 490.1 g (4.4 moles) of HDA was introduced for 1 hour. Upon completion of the introduction, the internal temperature of the reactor was lowered to 10° C., and it was stirred for 1 hour. Thereafter, 1,320.0 g of tetrahydrofuran was introduced, and the internal temperature of the reactor was lowered to −5° C., followed by stirring for 1 hour. Upon completion of the reaction, the diamine hydrochloride composition containing HDA·2HCl was separated by vacuum filtration using a filter, and the filtered tetrahydrofuran was recovered for reuse. Thereafter, the separated diamine hydrochloride composition was dried under vacuum at 90° C. and 0.5 torr to remove the residual solvent and water.

Step (2): Preparation of a Diisocyanate Composition

Reactor A was charged with 723 g of the diamine hydrochloride composition prepared above and 3,550 g of ODCB (Preparation Example A) whose water content had been adjusted to 200 ppm or less, followed by heating them at about 125° C. with stirring. Reactor B was charged with 950 g of triphosgene (BTMC) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 3 hours to 4 hours. Upon completion of the reaction, nitrogen gas was blown into the solvent with bubbling at 125° C. to degas. Thereafter, it was cooled to 10° C., and the remaining solids were filtered using celite to obtain a diisocyanate composition containing HDI. Thereafter, the organic solvent in the diisocyanate composition was removed, and distillation was carried out. Here, the removal of the organic solvent was carried out for 8 hours at a pressure of 0.5 torr or less and a temperature of 60° C. In addition, the distillation was carried out for 10 hours at a temperature of 120° C. and a pressure of 0.5 torr or less.

Example 1-7

Step (1): Preparation of a Diamine Hydrochloride Composition

Reactor 1 was charged with 1,009.4 g (9.46 moles) of an aqueous solution of 35% hydrochloric acid, followed by lowering the internal temperature of Reactor 1 to 15° C. with stirring. While the temperature of Reactor 1 was maintained at 50° C. or lower, 812.0 g (4.4 moles) of IPDA was introduced for 1 hour. Upon completion of the introduction, the internal temperature of Reactor 1 was lowered to 10° C., and it was stirred for 1 hour. The internal temperature of Reactor 2 to which 2,640.0 g of diethyl ether had been charged was lowered to −5° C. The mixture in Reactor 1 was slowly added dropwise to Reactor 2 at 0° C. or lower. Upon completion of the addition, the diamine hydrochloride composition containing IPDA 2HCl was separated by vacuum filtration using a filter, and the filtered diethyl ether was recovered for reuse. Thereafter, the separated diamine hydrochloride composition was dried under vacuum at 90° C. and 0.5 torr to remove the residual solvent and water.

Step (2): Preparation of a Diisocyanate Composition

Reactor A was charged with 984 g of the diamine hydrochloride composition prepared above and 3,550 g of ODCB (Preparation Example A) whose water content had been adjusted to 200 ppm or less, followed by heating them at about 125° C. with stirring. Reactor B was charged with 950 g of triphosgene (BTMC) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 3 hours to 4 hours. Upon completion of the reaction, nitrogen gas was blown into the solvent with bubbling at 125° C. to degas. Thereafter, it was cooled to 10° C., and the remaining solids were filtered using celite to obtain a diisocyanate composition containing IPDI. Thereafter, the organic solvent in the diisocyanate composition was removed, and distillation was carried out. Here, the removal of the organic solvent was carried out for 8 hours at a pressure of 0.5 torr or less and a temperature of 60° C. In addition, the distillation was carried out for 10 hours at a temperature of 120° C. and a pressure of 0.5 torr or less.

Comparative Examples 1-1 and 1-2

The same procedures as in Example 1-1 were repeated, except that, as the solvent used in step (2), ODCB (Preparation Example D or E) whose water content exceeded 200 ppm was used to prepare a diisocyanate composition.

Comparative Example 1-3

The same procedures as in Example 1-6 were repeated, except that, as the solvent used in step (2), ODCB (Preparation Example D) whose water content had not been adjusted was used to prepare a diisocyanate composition.

Comparative Example 1-4

The same procedures as in Example 1-7 were repeated, except that, as the solvent used in step (2), ODCB (Preparation Example D) whose water content had not been adjusted was used to prepare a diisocyanate composition.

Comparative Example 1-5

The same procedures as in Example 1-8 were repeated, except that, as the solvent used in step (2), ODCB (Preparation Example D) whose water content had not been adjusted was used to prepare a diisocyanate composition.

<Preparation of an Optical Lens>

As shown in Table 2 below, the diisocyanate composition (main component: m-XDI, H6XDI, HDI, or IPDI) prepared in the Examples or the Comparative Examples, 5,7-dimercaptomethyl-1,11-dimercapto-3,6-trithiaundecane (BET) as a polythiol, and a tin-based catalyst as an additive were uniformly mixed and defoamed at 600 Pa for 1 hour to prepare a polymerizable composition.

The polymerizable composition was filtered through a Teflon filter of 3 μm and injected into a glass mold assembled with an adhesive tape. The polymerizable composition injected into the mold was subjected to a first polymerized at a temperature of 10° C. to 35° C. for 3 hours to 9 hours, a second polymerization at a temperature of 35° C. to 60° C. for 3 hours to 9 hours, and a third polymerization at a temperature exceeding 60° C. for 2 hours to 7 hours. Upon completion of the polymerization, the plastic molded article (optical lens) was released from the mold and subjected to further curing at 130° C. for 2 hours.

BET:

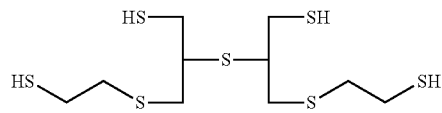 [SMILES: SCCSCC(CS)SC(CS)CSCCS]

5,7-dimercaptomethyl-1,11-dimercapto-3,6-trithiaundecane m-XDI:

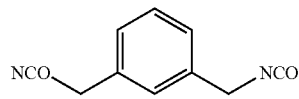

m-xylylene diisocyanate

H6XDI:

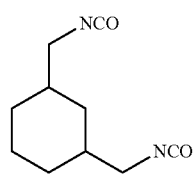

hydrogenated xylylene diisocyanate

HDI:

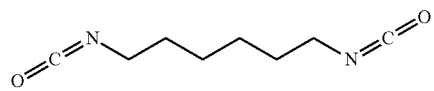 [SMILES: O=C=NCCCCCCN=C=O]

hexamethylene diisocyanate

IPDI:

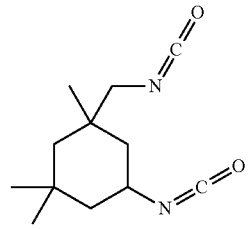 [SMILES: CC1(C)CC(N=C=O)CC(C)(CN=C=O)C1]

isophorone diisocyanate

TABLE 2

| | Polymerizable composition | | | |
|---|---|---|---|---|
| | Diisocyanate composition | | Polythiol | |
| Type | Part by weight | Main component | (BET) Part by weight | Additive Catalyst |
| Ex. 1-1 | 50.7 | m-XDI | 49.3 | 0.01 |
| Ex. 1-2 | 50.7 | m-XDI | 49.3 | 0.01 |
| Ex. 1-3 | 50.7 | m-XDI | 49.3 | 0.01 |
| Ex. 1-4 | 50.7 | m-XDI | 49.3 | 0.01 |
| Ex. 1-5 | 48.6 | H6XDI | 51.4 | 0.05 |
| Ex. 1-6 | 48.6 | HDI | 51.4 | 0.05 |
| Ex. 1-7 | 48.2 | IPDI | 54.8 | 0.05 |
| C. Ex. 1-1 | 50.7 | m-XDI | 49.3 | 0.01 |
| C. Ex. 1-2 | 50.7 | m-XDI | 49.3 | 0.01 |
| C. Ex. 1-3 | 48.6 | H6XDI | 51.4 | 0.05 |
| C. Ex. 1-4 | 48.6 | HDI | 51.4 | 0.05 |
| C. Ex. 1-5 | 48.2 | IPDI | 54.8 | 0.05 |

<Evaluation Method>

The Examples and the Comparative Examples were evaluated as follows.

(1) Content of a Diisocyanate

The content of a diisocyanate in the diisocyanate composition was determined by gas chromatography (GC) (instrument: 6890/7890 of Agilent, carrier gas: He, injection temperature 250° C., oven temperature 40° C. to 320° C., column: HP-1, Wax, 30 m, detector: FID, 300° C.)

(2) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(3) Yellow Index (Y.I.)

An optical lens was prepared in the form of a cylinder with a radius of 16 mm and a height of 45 mm. Light was transmitted in the height direction to measure the yellow index. The yellow index was calculated by the following equation based on the values of x and y, which are the measurement results. Y.I.=(234x+106y)/y.

(4) Cloudiness (Haze)

The optical lens was irradiated to a projector in a darkroom to observe whether the optical lens was cloudy or had any opaque material with the naked eyes.

TABLE 3

| | Organic solvent (ODCB) | Distillation yield (%) | Content of a diisocyanate in the diisocyanate composition (% by weight) | | Optical lens | | |
|---|---|---|---|---|---|---|---|
| | | | Before distillation | After distillation | Stria | Cloudiness | Y.I. |
| Ex. 1-1 | Prep. Ex. A | 89 | 99.4 | 99.9 | Absent | Absent | 19 |
| Ex. 1-2 | Prep. Ex. B | 91 | 99.4 | 99.9 | Absent | Absent | 20 |
| Ex. 1-3 | Prep. Ex. C | 89 | 99.5 | 99.9 | Absent | Absent | 19 |
| Ex. 1-4 | Prep. Ex. F | 90 | 99.5 | 99.9 | Absent | Absent | 19 |
| Ex. 1-5 | Prep. Ex. A | 89 | 99.3 | 99.8 | Absent | Absent | 20 |
| Ex. 1-6 | Prep. Ex. A | 89 | 99.5 | 99.8 | Absent | Absent | 19 |
| Ex. 1-7 | Prep. Ex. A | 89 | 99.4 | 99.7 | Absent | Absent | 19 |
| C. Ex. 1-1 | Prep. Ex. D | 82 | 98.2 | 99.5 | Absent | Slight haze | 24 |
| C. Ex. 1-2 | Prep. Ex. E | 85 | 98.9 | 99.8 | Absent | Slight haze | 22 |
| C. Ex. 1-3 | Prep. Ex. D | 85 | 98.3 | 99.2 | Absent | Slight haze | 23 |
| C. Ex. 1-4 | Prep. Ex. D | 82 | 98.1 | 99.3 | Absent | Slight haze | 24 |
| C. Ex. 1-5 | Prep. Ex. D | 83 | 98.0 | 99.3 | Absent | Slight haze | 23 |

As can be seen from the above table, in Examples 1-1 to 1-7 in which a solvent whose water content had been adjusted to 200 ppm or less was used in the reaction of the diamine hydrochloride composition and triphosgene, the distillation yield and the content of a diisocyanate in the composition were excellent. The optical lenses prepared therefrom were improved in stria, cloudiness, and yellow index.

In contrast, in Comparative Examples 1-1 and 1-5 in which a solvent whose water content exceeded 200 ppm was used, the distillation yield and the content of a diisocyanate in the composition were poor. The optical lenses prepared therefrom had cloudiness and yellowing.

Example 2-1

<Step 1: Preparation of a Diamine Hydrochloride Composition>

A 5-liter, 4-neck reactor was charged with 1009.4 g (9.46 moles) of an aqueous solution of 35% hydrochloric acid, followed by lowering the internal temperature of the reactor to 15° C. with stirring. While the temperature of the reactor was maintained at lower than 60° C., 600.0 g (4.4 moles) of metaxylylenediamine (m-XDA) was introduced for 1 hour. Upon completion of the introduction, the internal temperature of the reactor was lowered to 10° C., and it was stirred for 1 hour. Thereafter, 1,320 g of tetrahydrofuran as a first organic solvent was introduced, and the internal temperature of the reactor was lowered to −5° C., followed by stirring for 1 hour. Upon completion of the reaction, it was subjected to vacuum filtration using a filter, and the filtered tetrahydrofuran was recovered for reuse. The recovery rate of the tetrahydrofuran was 82%. Upon the vacuum filtration, a metaxylylenediamine (m-XDA) hydrochloride composition was obtained. In order to remove the residual organic solvent and water, drying was performed under the conditions of a reactor external temperature of 90° C. and a vacuum pump of 0.1 Torr to obtain a final metaxylylenediamine (m-XDA) hydrochloride composition.

<Step 2: Preparation of a Diisocyanate Composition>

The content of an aromatic compound containing 3 or more of chlorine (Cl) in 1,2-dichlorobenzene (ODCB) (for industrial use not recycled) as an organic solvent (second organic solvent) was measured by gas chromatography (GC). As a result of the measurement, the content of 1,2,3-trichlorobenzene in ODCB was less than 10 ppm as shown in Table 4 below. It was used in the reaction.

Reactor A was charged with 800 g of the m-XDA hydrochloride prepared in step 1 above and 3,550 g of 1,2-dichlorobenzene (ODCB), followed by elevating the internal temperature of the reactor to about 125° C. with stirring. Reactor B was charged with 950 g of triphosgene (BTMC) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas. It was cooled to 10° C., and the remaining solids were filtered using celite. Thereafter, the second organic solvent (ODCB) was removed, and m-XDI was purified by distillation under the following distillation conditions. The removal of the second organic solvent (first distillation) was carried out for 8 hours at a pressure of 0.5 torr or less and a temperature of 60° C. The distillation of m-XDI (second distillation) was carried out for 10 hours at a pressure of 0.1 torr or less and a temperature of 120° C.

<Preparation of an Optical Material>

49.3 parts by weight of 4,8-bis(mercaptomethyl)-3,6,9-trithiaundecane-1,11-dithiol, 50.7 parts by weight of the m-XDI composition prepared above, 0.01 part by weight of dibutyltin dichloride, and 0.1 part by weight of a phosphate ester release agent (ZELEC® UN Stepan) were homogeneously mixed, which was defoamed at 600 Pa for 1 hour, filtered through a Teflon filter of 3 μm, and injected into a mold made of a glass mold and a tape. The mold was maintained at 25° C. for 8 hours and slowly heated to 130° C. at a constant rate over 8 hours, and polymerization was carried out at 130° C. for 2 hours. The molded article was released from the mold and subjected to further curing at 120° C. for 2 hours to obtain an optical lens (or an optical material).

Examples 2-2 and 2-3

A m-XDI composition and an optical lens were obtained in the same manner as in Example 2-1, except that 1,2-dichlorobenzene (ODCB) (recycled 5 times) having a content of 1,2,3-trichlorobenzene as shown in Table 4 below was used.

Example 2-4 and 2-5

A m-XDI composition and an optical lens were obtained in the same manner as in Example 2-1, except that 1,2-dichlorobenzene (ODCB) (recycled 10 times or more) having a content of 1,2,3-trichlorobenzene as shown in Table 4 was purified under the conditions of about 60° C. and 0.5 tory to adjust the content of 1,2,3-trichlorobenzene to less than 10 ppm and then used.

Comparative Examples 2-1 and 2-2

A m-XDI composition and an optical lens were obtained in the same manner as in Example 2-1, except that 1,2-dichlorobenzene (ODCB) (recycled 10 times or more) having a content of 1,2,3-trichlorobenzene as shown in Table 4 below was used.

<Evaluation Method>

The Examples and the Comparative Examples were evaluated as follows.

(1) Yellow Index (Y.I.) and Light Transmittance

A UV/VIS Spectroscopy (PerkinElmer, model UV/VIS Lambda 365) was used to transmit light in the height direction of a plastic cylinder (r (radius)×H (height)=16 mm×45 mm) to measure the yellow index (Y.I.) and transmittance.

The yellow index (Y.I.) was calculated by the following Equation 1 based on the values of x and y, which are the measurement results.

$$Y.I.=(234x+106y+106)/y \quad \text{[Equation 1]}$$

(2) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(3) Cloudiness

The cured lens was irradiated to a projector in a darkroom to observe whether the lens was cloudy or had any opaque material with the naked eyes.

No cloudiness: the lens was not cloudy and had no opaque material

Cloudiness: the lens was cloudy or had an opaque material (4) Measurement of the Content of 1,2,3-Trichlorobenzene in an Organic Solvent (Second Organic Solvent)

In order to measure the content of 1,2,3-trichlorobenzene in ODCB, each ODCB used in the Examples and the Comparative Examples was measured by gas chromatography (GC).

<Measurement of Gas Chromatography (GC)>
6890/7890 of Agilent
Carrier gas: He
Injector: 250° C.
Oven: 40° C. to 320° C.
Column: HP-1, Wax, 30 m
Detector: FID, 300° C.

<Measurement of GC MS>
7890B (GC), 5977A (MS) of Agilent
Mass range: 1.6 amu to 1,050 amu
Source: EI (electron ionization) (inert extractor EI source)
Mass spectrometer: quadrupole spectrometer
Oven: 40° C. (6 min)−10° C./min−140° C. (5 min)−15° C./min−290° C. (15 min)
Column: Rxi-5MS, ID 0.25 mm, L 30 m The graphs of the GC results of 1,2-dichlorobenzene (ODCB) used in Example 2-1 and Comparative Example 2-1 are shown in FIGS. 3 and 4. The specific values for the respective peaks related thereto are shown in Table 4 below. In addition, the results measured by the above evaluation methods are summarized in Tables 5 to 7 below.

TABLE 4

| | Peak No. | Retention time (minute) | Width (minute) | Area (pA * s) | Height (pA) | Area (%) |
|---|---|---|---|---|---|---|
| Ex. 2-1 | 1 | 5.498 | 0.028 | 4465.84 | 2690.17 | 100.00 |
| C. Ex. 2-1 | 1 | 5.498 | 0.028 | 4441.63 | 2676.49 | 98.88 |
| | 2 | 6.282 | 0.104 | 18.08 | 2.90 | 0.40 |
| | 3 | 6.740 | 0.132 | 32.24 | 4.06 | 0.72 |

TABLE 5

| | ODCB | |
|---|---|---|
| | Content of 1,2,3-trichlorobenzene | Content of 1,2,3-trichlorobenzene after distillation |
| Ex. 2-1 | <10 ppm | No distillation |
| Ex. 2-2 | 2,510 ppm | No distillation |
| Ex. 2-3 | 4,900 ppm | No distillation |
| Ex. 2-4 | 5,520 ppm | <10 ppm |
| Ex. 2-5 | 12,150 ppm | <10 ppm |
| C. Ex. 2-1 | 5,520 ppm | No distillation |
| C. Ex. 2-2 | 7,200 ppm | No distillation |

TABLE 6

| | Physical properties of the diisocyanate composition | | |
|---|---|---|---|
| | Purity of the crude product | Distillation yield | Final purity |
| Ex. 2-1 | 99.1 | 91% | 92% |
| Ex. 2-2 | 99.2 | 90% | 91% |
| Ex. 2-3 | 99.1 | 92% | 85% |
| Ex. 2-4 | 99.2 | 90% | 91% |
| Ex. 2-5 | 99.1 | 91% | 91% |
| C. Ex. 2-1 | 98.5 | 85% | 91% |
| C. Ex. 2-2 | 98.4 | 82% | 91% |

TABLE 7

| | Physical properties of the optical lens | | | |
|---|---|---|---|---|
| | Stria | Cloudiness | Transmittance | Y.I. (yellow index) |
| Ex. 2-1 | Absent | Absent | 90 | 19 |
| Ex. 2-2 | Absent | Absent | 91 | 20 |
| Ex. 2-3 | Absent | Absent | 89 | 20 |
| Ex. 2-4 | Absent | Absent | 91 | 19 |
| Ex. 2-5 | Absent | Absent | 91 | 19 |
| C. Ex. 2-1 | Absent | Slight cloudiness | 90 | 23 |
| C. Ex. 2-2 | Absent | Slight cloudiness | 87 | 24 |

As can be seen from the above tables, in Examples 2-1 to 2-5 in which an aromatic compound containing 3 or more of chlorine (Cl) in ODCB was adjusted to 5,000 ppm or less, the purity and yield of the diisocyanate compositions were enhanced, so that their quality was excellent. The optical lenses prepared therefrom were excellent in transmittance as compared with the optical lenses of the Comparative Examples, and they had no striae and cloudiness.

First, the ODCB used in the preparation of the diisocyanate compositions of Examples 2-1 to 2-5 had 5,000 ppm or less of 1,2,3-trichlorobenzene. In particular, as shown in FIG. 3, the ODCB used in Example 2-1 had only a peak for ODCB (the peak marked as "1" in FIGS. 3 and 4) was present, and the peak for 1,2,3-trichlorobenzene (the peak marked as "3" in FIG. 4) was not present.

Specifically, referring to FIGS. 3 and 4 and Table 4, in Example 2-1, the area of the peak for ODCB (the peak marked as "1") was 100%. In contrast, in Comparative Example 2-1, the area of the peak for ODCB (the peak marked as "1") was 98.88%, the area of the peak for 1,2,3-trichlorobenzene (the peak marked as "3") was 0.72%, and the area of the other peak (the peak marked as "2") was 0.40%. In addition, for the peak for ODCB (peak marked as "1") in Example 2-1, the retention time was about 5.498 (minutes), the width was 0.028 (minutes), the height was 2,690.17 (pA), and the area represented by the product of height and width (pA*s) was 4,465.84. In contrast, for the peak for ODCB (peak marked as "1") in Comparative Example 2-1, the retention time and width were the same as those of Example 2-1, whereas the height was 2,676.49 (pA), and the area represented by the product of height and width (pA*s) was 4,441.63, which were reduced as compared with Example 2-1.

As described above, the diisocyanate compositions using ODCB in which the content of 1,2,3-trichlorobenzene had been adjusted were all 90% or more in yield and 99.9% or more in purity, so that they were very excellent in quality.

In addition, the optical lenses prepared using the diisocyanate compositions of Examples 2-1 to 2-5 had no striae and cloudiness, a high transmittance of 90% or more, a low yellow index of 20 or lower.

Further, even if recycled ODCB having a content of an aromatic compound containing 3 or more of chlorine (Cl) exceeding 5,000 ppm was used, it was possible to obtain a diisocyanate composition and an optical lens of excellent quality when the above content was adjusted by purification.

In contrast, as shown in FIG. 4, in Comparative Example 2-1 in which ODCB having a content of 1,2,3-trichlorobenzene exceeding 5,000 ppm was not purified, the peak for 1,2,3-trichlorobenzene in ODCB (the peak marked as "3" in FIG. 4) clearly appeared.

In addition, in Comparative Examples 2-1 and 2-2 in which ODCB having a content of 1,2,3-trichlorobenzene exceeding 5,000 ppm was used, the purity and yield of the diisocyanate compositions were significantly inferior to Examples 2-1 to 2-5. The optical lenses prepared therefrom had cloudiness and a transmittance of 90% or lower and a yellow index of 23 or more, showing poor optical characteristics as compared with the optical lenses of Examples 2-1 to 2-5.

Accordingly, the diisocyanate composition according to an embodiment of the present invention is excellent in optical characteristics when applied to an optical lens. Thus, it is suitable for use as an optical material of high quality.

Example 3-1

<Step 1: Preparation of a Diamine Hydrochloride Composition>

A 5-liter, 4-neck reactor was charged with 1009.4 g (9.46 moles) of an aqueous solution of 35% hydrochloric acid, followed by lowering the internal temperature of the reactor to 15° C. with stirring. While the temperature of the reactor was maintained at lower than 60° C., 600.0 g (4.4 moles) of metaxylylenediamine (m-XDA) was introduced for 1 hour. Upon completion of the introduction, the internal temperature of the reactor was lowered to 10° C., and it was stirred for 1 hour. Thereafter, 1,320 g of tetrahydrofuran as a first organic solvent was introduced, and the internal temperature of the reactor was lowered to −5° C., followed by stirring for 1 hour. Upon completion of the reaction, it was subjected to vacuum filtration using a filter, and the filtered tetrahydrofuran was recovered for reuse. The recovery rate of the tetrahydrofuran was 82%. Upon the vacuum filtration, a metaxylylenediamine (m-XDA) hydrochloride composition was obtained. In order to remove the residual organic solvent and water, drying was performed under the conditions of a reactor external temperature of 90° C. and a vacuum pump of 0.1 Torr to obtain a final metaxylylenediamine (m-XDA) hydrochloride composition.

<Step 2: Preparation of a Diisocyanate Composition>

The total content of cations in 1,2-dichlorobenzene (ODCB) (for industrial use not recycled) as an organic solvent (second organic solvent) was measured by ion chromatography (IC). As a result of the measurement, the total content of cations in ODCB was 4.2 ppm as shown in Table 8 below. It was used in the reaction.

Reactor A was charged with 800 g of the m-XDA hydrochloride prepared in step 1 above and 3,550 g of 1,2-dichlorobenzene (ODCB), followed by elevating the internal temperature of the reactor to about 125° C. with stirring. Reactor B was charged with 950 g of triphosgene (BTMC) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas. It was cooled to 10° C., and the remaining solids were filtered using celite. Thereafter, the second organic solvent (ODCB) was removed, and m-XDI was purified by distillation under the following distillation conditions. The removal of the second organic solvent (first distillation) was carried out for 8 hours at a pressure of 0.5 torr or less and a temperature of 60° C. The distillation of m-XDI (second distillation) was carried out for 10 hours at a pressure of 0.1 torr or less and a temperature of 120° C.

<Preparation of an Optical Material>

49.3 parts by weight of 4,8-bis(mercaptomethyl)-3,6,9-trithiaundecane-1,11-dithiol, 50.7 parts by weight of the m-XDI composition prepared above, 0.01 part by weight of dibutyltin dichloride, and 0.1 part by weight of a phosphate ester release agent (ZELEC® UN Stepan) were homogeneously mixed, which was defoamed at 600 Pa for 1 hour, filtered through a Teflon filter of 3 μm, and injected into a mold made of a glass mold and a tape. The mold was maintained at 25° C. for 8 hours and slowly heated to 130° C. at a constant rate over 8 hours, and polymerization was carried out at 130° C. for 2 hours. The molded article was released from the mold and subjected to further curing at 120° C. for 2 hours to obtain an optical lens (or an optical material).

Example 3-2

A m-XDI composition and an optical lens were obtained in the same manner as in Example 3-1, except that 1,2-dichlorobenzene (ODCB) (recycled 5 times) having a total content of cations as shown in Table 8 below was used.

Examples 3-3 and 3-4

A m-XDI composition and an optical lens were obtained in the same manner as in Example 3-1, except that 1,2-dichlorobenzene (ODCB) (recycled 10 times or more) having a total content of cations as shown in Table 8 was purified under the conditions of about 60° C. and 0.5 torr to adjust the total content of cations to less than 5 ppm and then used.

Comparative Examples 3-1 and 3-2

A m-XDI composition and an optical lens were obtained in the same manner as in Example 3-1, except that 1,2-dichlorobenzene (ODCB) (recycled 10 times or more) having a total content of cations as shown in Table 8 below was used without purification.

<Evaluation Method>

The Examples and the Comparative Examples were evaluated as follows.

(1) Measurement of the Total Content of Cations in an Organic Solvent (Second Organic Solvent)

In order to measure the total content of cations in ODCB, each ODCB used in the Examples and the Comparative Examples was measured by ion chromatography (IC).

<Measurement of Ion Chromatography (IC)>

Measurement instrument: ion chromatography (IC)

Model name: Metrohm 882 Compact IC Plus

Sample pretreatment: for a liquid sample, 2 g thereof was sonicated in 18 g of water for 1 hour, and the aqueous layer was collected. For a solid sample, a solution in which 0.2 g thereof was dissolved in 19.8 g of water was prepared.

(2) Measurement of the Content of a Diisocyanate

The content of a diisocyanate in the diisocyanate composition was determined by gas chromatography (GC) (instrument: 6890/7890 of Agilent, carrier gas: He, injection temperature 250° C., oven temperature 40° C. to 320° C., column: HP-1, Wax, 30 m, detector: FID, 300° C.)

(3) Yellow Index (Y.I.) and Light Transmittance

A UV/VIS Spectroscopy (PerkinElmer, model UV/VIS Lambda 365) was used to transmit light in the height direction of a plastic cylinder (r (radius)×H (height)=16 mm×45 mm) to measure the yellow index (Y.I.) and transmittance.

The yellow index (Y.I.) was calculated by the following Equation 2 based on the values of x and y, which are the measurement results.

$$Y.I.=(234x+106y+106)/y \qquad \text{[Equation 2]}$$

(4) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(5) Refractive Index (Nd20)

The solid-phase refractive index (nd20) was measured at 20° C. using an Abbe refractometer DR-M4.

(6) Measurement of Polymerization Rate (Reactivity)

The change in viscosity of the polymerizable composition with respect to time was measured at 10° C. using a non-contact viscometer (EMS-1000, Kyoto Electronics Manufacturing Co., Ltd.). Here, the polymerization rate was calculated as the slope when the graph was linearized with the X-axis as time and the Y-axis as the logarithm of the viscosity. Specifically, the rate of change (b) of the viscosity (Y) over time (X) of the polymerizable composition was derived using Equation 1, which was rounded to the third decimal place.

$$Y=a \times \exp(b \times X) \qquad \text{[Equation 1]}$$

In the above equation, Y is the viscosity (cPs) of the polymerizable composition, X is the time (hr) elapsed after the preparation of the polymerizable composition, for example, a variable from 5 to 24, and a is a constant, which refers to the initial viscosity (cPs), may be determined between, for example, 20 and 1,000 depending on the polymerization conditions, and does not affect the determination of the b value.

TABLE 8

Content of cations in the second organic solvent (ODCB)

| | Na⁺ (ppm) (before distillation/after distillation) | K⁺ (ppm) (before distillation/after distillation) | NH₄⁺ (ppm) (before distillation/after distillation) | Total content of cations (ppm) (before distillation/ after distillation) | Distillation yield |
|---|---|---|---|---|---|
| Ex. 3-1 | 3.6 | 0.3 | 0.3 | 4.2 (no distillation) | 92% |
| Ex. 3-2 | 4.1 | 0.3 | 0.3 | 4.7 (no distillation) | 91% |
| Ex. 3-3 | 5.4/3.8 | 0.4/0.3 | 0.4/0.3 | 6.2/4.1 | 87% |
| Ex. 3-4 | 6.5/4.2 | 0.5/0.3 | 0.5/0.3 | 7.5/4.8 | 89% |
| C. Ex. 3-1 | 5.4 | 0.4 | 0.4 | 6.2 (no distillation) | — |
| C. Ex. 3-2 | 6.5 | 0.5 | 0.5 | 7.5 (no distillation) | — |

TABLE 9

Physical properties of the diisocyanate composition

| | Purity of the crude product | Total content of cations after distillation (ppm) | Distillation yield | Final purity |
|---|---|---|---|---|
| Ex. 3-1 | 99.2% | 22 | 91% | 91% |
| Ex. 3-2 | 99.3% | 45 | 90% | 91% |
| Ex. 3-3 | 99.2% | 23 | 90% | 91% |
| Ex. 3-4 | 99.1% | 75 | 90% | 99.9% |
| C. Ex. 3-1 | 98.5% | 115 | 88% | 99.7% |
| C. Ex. 3-2 | 98.5% | 152 | 86% | 91% |

TABLE 10

Physical properties of the optical lens

| | Reactivity Polymerization rate (b value) | Stria | Transmittance | Y.I. (yellow index) | Refractive index |
|---|---|---|---|---|---|
| Ex. 3-1 | 0.18 | Absent | 91 | 18 | 1.670 |
| Ex. 3-2 | 0.23 | Absent | 91 | 20 | 1.670 |
| Ex. 3-3 | 0.20 | Absent | 90 | 20 | 1.670 |
| Ex. 3-4 | 0.20 | Absent | 90 | 20 | 1.670 |
| C. Ex. 3-1 | 0.32 | Present | 88 | 22 | 1.670 |
| C. Ex. 3-2 | 0.35 | Present | 88 | 22 | 1.670 |

As can be seen from the above tables, in Examples 3-1 to 3-4 in which the total content of cations in ODCB was adjusted to 1 ppm to 5 ppm, the quality and yield of the diisocyanate compositions were excellent, and an appropriate polymerization reaction could be achieved when an optical lens was prepared since the total content of cations in the composition was small. In addition, the optical lenses prepared therefrom in Examples 3-1 to 3-4 were excellent in transmittance as compared with the optical lenses of Comparative Examples 3-1 and 3-2, and they had no striae.

Specifically, ODCB used in the preparation of the diisocyanate compositions of Examples 3-1 to 3-4 all had a total content of cations of 1 ppm to 5 ppm. It contained Na⁺, K⁺, and NH₄⁺, as the kind of the cations, in an appropriate content range.

As described above, the diisocyanate compositions using ODCB in which the total content of cations had been adjusted were all 90% or more in yield and 99.9% or more in purity, so that they were very excellent in quality.

In addition, when optical lenses were prepared using the diisocyanate compositions of Examples 3-1 to 3-4, the reactive polymerization rate (b) was appropriate as 0.18 to 0.23, securing an appropriate rate of polymerization reaction. The optical lenses thus prepared were excellent in stria, transmittance, yellowness, and refractive index. Further, even if recycled ODCB having a total content of cations exceeding 5 ppm was used, it was possible to obtain a diisocyanate composition and an optical lens of excellent quality when the content of cations was adjusted by purification to a desired range in the present invention.

In contrast, in Comparative Examples 2-1 and 2-2 in which ODCB having a total content of cations exceeding 5 ppm was used, the purity and yield of the diisocyanate compositions were inferior to Examples 3-1 to 3-4. In addition, when optical lenses were prepared therefrom, the reactive polymerization rate (b) exceeded 0.3, so that the rate of polymerization reaction was very fast. The optical lenses thus prepared had striae and a transmittance of 90% or lower and a yellow index of 22, showing poor optical characteristics as compared with the optical lenses of Examples 3-1 to 3-4.

Accordingly, the diisocyanate composition according to an embodiment of the present invention is excellent in optical characteristics when applied to an optical lens. Thus, it is suitable for use as an optical material of high quality.

The invention claimed is:

1. A process for preparing a diisocyanate composition, which comprises:
   (1) reacting a diamine with an aqueous hydrochloric acid solution to obtain a diamine hydrochloride composition; and
   (2) reacting the diamine hydrochloride composition with triphosgene in an organic solvent to obtain a diisocyanate composition,
   wherein, a content of water, or a content of an aromatic compound containing 3 or more of chlorine (Cl) in the organic solvent is adjusted,
   wherein further comprising measuring a total content of cations in the organic solvent before the reaction, wherein, if the total content of cations in the organic solvent exceeds 5 ppm, the organic solvent is purified and then used in the reaction,
   and wherein, when the organic solvent is purified, the content of cations in the organic solvent is adjusted.

2. The process for preparing the diisocyanate composition of claim 1, wherein the content of water in the organic solvent is adjusted to 200 ppm or less.

3. The process for preparing the diisocyanate composition of claim 1, wherein after the adjustment the organic solvent comprises 1,2-dichlorobenzene (ODCB), and the organic solvent comprises an aromatic compound containing 3 or more of chlorine (Cl) in an amount of 5,000 ppm or less.

4. The process for preparing the diisocyanate composition of claim 1, wherein the content of water in the organic solvent is adjusted by dehydration under a reduced pressure, the dehydration is performed for 1 hour to 3 hours at a temperature of 20° C. to 40° C. and a pressure of 0.5 torr or less, the dehydration is performed at a yield of 90% or more removing 90% of the water in the organic solvent, and the content of water in the organic solvent is 100 ppm or less after the dehydration.

5. The process for preparing the diisocyanate composition of claim 1, which further comprises measuring the content of water in the organic solvent before step (2), wherein, if the content of water in the organic solvent exceeds 200 ppm, the content of water is adjusted by dehydration under a reduced pressure.

6. The process for preparing the diisocyanate composition of claim 1, wherein the diisocyanate composition is obtained by distillation after the reaction of the diamine hydrochloride composition and triphosgene, the distillation comprises distillation of a diisocyanate at a temperature of 100° C. to 130° C. and a pressure of 2 torr or less, the yield of the distillation of a diisocyanate is 85% or more, and the diisocyanate composition comprises the diisocyanate in an amount of 99.9% by weight or more after the distillation of a diisocyanate.

7. The process for preparing the diisocyanate composition of claim 1, wherein, after the adjustment, the aromatic compound containing 3 or more of chlorine (Cl) comprises a mixture of 1,2,3-trichlorobenzene, 1,2,4-trichlorobenzene, at a weight ratio of 1,2,3-trichlorobenzene and 1,2,4-trichlorobenzene of 1:0.0001 to 0.5.

8. The process for preparing the diisocyanate composition of claim 1, which further comprises measuring the content of an aromatic compound containing 3 or more of chlorine (Cl) in the organic solvent before the reaction, wherein, if the content of an aromatic compound containing 3 or more of chlorine (Cl) contained in the organic solvent exceeds 5,000 ppm, the organic solvent is purified and then used in the reaction.

9. The process for preparing the diisocyanate composition of claim 8, wherein the purification comprises a purification process by first distillation under the conditions of a temperature of 45° C. to 75° C. and a pressure of 0.1 torr to 1 torr, and the content of an aromatic compound containing 3 or more of chlorine (Cl) in the organic solvent after the purification is 100 ppm or less.

10. The process for preparing the diisocyanate composition of claim 1, wherein, after the adjustment, the cations comprise a monovalent cation, which comprises $Na^+$, $K^+$, and $NH_4^+$, the content of $Na^+$ is 0.8 ppm to 4.8 ppm, the content of $K^+$ is 0.1 ppm to 1 ppm, the content of $NH_4^+$ is 0.1 ppm to 1 ppm, the weight ratio of $Na^+$ and $K^+$ is 1:0.02 to 0.2, and the weight ratio of $Na^+$ and $NH_4^+$ is 1:0.02 to 0.2.

11. The process for preparing the diisocyanate composition of claim 1, which further comprises treating the diamine hydrochloride composition by at least one of precipitation, filtration, drying, and washing before the diamine hydrochloride composition is reacted with triphosgene.

* * * * *